US008715732B2

(12) United States Patent
Luo et al.

(10) Patent No.: US 8,715,732 B2
(45) Date of Patent: May 6, 2014

(54) NUCLEIC ACID HYDROGEL VIA ROLLING CIRCLE AMPLIFICATION

(75) Inventors: Dan Luo, Ithaca, NY (US); Jong Bum Lee, Ithaca, NY (US); Hisakage Funabashi, Koganei (JP)

(73) Assignee: Cornell University, Ithaca, NY (US)

( * ) Notice: Subject to any disclaimer, the term of this patent is extended or adjusted under 35 U.S.C. 154(b) by 497 days.

(21) Appl. No.: 12/652,707

(22) Filed: Jan. 5, 2010

(65) Prior Publication Data
US 2010/0189794 A1 Jul. 29, 2010

Related U.S. Application Data

(60) Provisional application No. 61/204,385, filed on Jan. 5, 2009.

(51) Int. Cl.
*A61K 9/14* (2006.01)
*A61J 3/00* (2006.01)

(52) U.S. Cl.
USPC .................................. 424/484; 424/486; 264/4

(58) Field of Classification Search
None
See application file for complete search history.

(56) References Cited

U.S. PATENT DOCUMENTS

| 5,445,934 | A | 8/1995 | Fodor et al. |
|---|---|---|---|
| 5,610,289 | A | 3/1997 | Cook et al. |
| 5,797,801 | A | 8/1998 | Jacob |
| 5,885,829 | A | 3/1999 | Mooney et al. |
| 5,965,721 | A | 10/1999 | Cook et al. |
| 6,025,482 | A | 2/2000 | Cook et al. |
| 6,201,103 | B1 | 3/2001 | Nielsen et al. |
| 6,419,709 | B1 | 7/2002 | Mao et al. |
| 6,572,605 | B1 | 6/2003 | Humes |
| 6,585,763 | B1 | 7/2003 | Keilman et al. |
| 6,846,625 | B1 | 1/2005 | Tally et al. |
| 6,855,504 | B2 | 2/2005 | Fogarty |
| 6,902,881 | B2 | 6/2005 | Falchuk |
| 6,951,757 | B2 | 10/2005 | Sabatini |
| 6,962,980 | B2 | 11/2005 | Mitcham et al. |
| 6,963,771 | B2 | 11/2005 | Scarantino et al. |
| 6,965,798 | B2 | 11/2005 | Kim |
| 6,972,195 | B2 | 12/2005 | Xu |
| 6,982,168 | B1 | 1/2006 | Topalian et al. |
| 7,006,870 | B1 | 2/2006 | Whitehurst et al. |
| 7,008,634 | B2 | 3/2006 | Cima et al. |
| 7,008,667 | B2 | 3/2006 | Chudzik et al. |
| 7,013,177 | B1 | 3/2006 | Whitehurst et al. |
| 7,179,638 | B2 | 2/2007 | Anderson et al. |
| 7,354,706 | B2 | 4/2008 | Rowlen et al. |
| 7,442,506 | B2 | 10/2008 | Dhallan |
| 7,473,551 | B2 | 1/2009 | Warthoe |
| 7,531,305 | B2 | 5/2009 | Thunnissen et al. |
| 2001/0049436 | A1 | 12/2001 | Zhou et al. |
| 2002/0006664 | A1 | 1/2002 | Sabatini |
| 2003/0022231 | A1* | 1/2003 | Wangh et al. ............. 435/6 |
| 2003/0044855 | A1 | 3/2003 | Anderson et al. |
| 2003/0054355 | A1 | 3/2003 | Warthoe |
| 2003/0203486 | A1 | 10/2003 | Sabatini |
| 2003/0224395 | A1 | 12/2003 | Jovanovich et al. |
| 2003/0228601 | A1 | 12/2003 | Sabatini |
| 2003/0228694 | A1 | 12/2003 | Sabatini |
| 2004/0014078 | A1 | 1/2004 | Xia et al. |
| 2004/0109853 | A1 | 6/2004 | Mcdaniel |
| 2004/0161844 | A1 | 8/2004 | Baker et al. |
| 2004/0241759 | A1 | 12/2004 | Tozer et al. |
| 2005/0025797 | A1 | 2/2005 | Wang et al. |
| 2005/0032068 | A1 | 2/2005 | Prakash et al. |
| 2005/0079132 | A1 | 4/2005 | Wang et al. |
| 2005/0107870 | A1 | 5/2005 | Wang et al. |
| 2005/0147973 | A1 | 7/2005 | Knott |
| 2005/0164283 | A1* | 7/2005 | Krotz et al. ............. 435/6 |
| 2006/0024813 | A1 | 2/2006 | Warthoe |
| 2006/0121452 | A1 | 6/2006 | Dhallan |
| 2006/0160105 | A1 | 7/2006 | Dhallan |
| 2006/0286570 | A1 | 12/2006 | Rowlen et al. |
| 2007/0010702 | A1 | 1/2007 | Wang et al. |
| 2007/0048759 | A1 | 3/2007 | Luo et al. |
| 2007/0068824 | A1 | 3/2007 | Payne et al. |
| 2007/0117177 | A1 | 5/2007 | Luo et al. |
| 2007/0148246 | A1 | 6/2007 | Luo et al. |
| 2007/0148639 | A1 | 6/2007 | Chagovetz et al. |
| 2007/0178478 | A1 | 8/2007 | Dhallan et al. |
| 2007/0275246 | A1 | 11/2007 | Payne et al. |
| 2008/0009420 | A1 | 1/2008 | Schroth et al. |
| 2008/0076131 | A1 | 3/2008 | Chagovetz et al. |
| 2008/0153081 | A1 | 6/2008 | Thunnissen et al. |
| 2009/0093378 | A1 | 4/2009 | Bignell et al. |
| 2009/0137405 | A1 | 5/2009 | Bowman et al. |
| 2009/0142752 | A1 | 6/2009 | Hall et al. |
| 2009/0163375 | A1 | 6/2009 | Bowman et al. |

(Continued)

FOREIGN PATENT DOCUMENTS

WO WO 2010/017264 A2 2/2010
WO WO 2010/017264 A3 5/2010

OTHER PUBLICATIONS

Lizardi et al., Nature Genetics, 1998; 19:225-232.*
U.S. Appl. No. 60/783,426, filed Mar. 17 2006, Luo et al.
Altschul, et al. Gapped BLAST and PSI-BLAST: a new generation of protein database search programs. Nucl. Acids. Res. 1990; 25:3389-3402.
Becker, et al. Molecular nanosprings in spider capture-silk threads. Nat Mater. Apr. 2003;2(4):278-83.
Corpet. Multiple sequence alignment with hierarchical clustering. Nucl. Acids. Res. 1988; 16:10881-90.
Karlin, et al. Methods for assessing the statistical significance of molecular sequence features by using general scoring schemes. Procs. Natl. Acad. Sci. USA. 1990; 87:2264-2268.
Karlin, et al. Applications and statistics for multiple high-scoring segments in molecular sequences. Proc Natl Acad Sci U S A. Jun. 15, 1993;90(12):5873-7.

(Continued)

*Primary Examiner* — Doug Schultz
(74) *Attorney, Agent, or Firm* — Wilson Sonsini Goodrich & Rosati

(57) ABSTRACT

Methods and compositions are provided for producing nucleic acid-based compositions. Methods include enzyme catalyzed or nucleic acid polymer conjugation. Compositions include nucleic acid-containing hydrogels which can be elongated via rolling circle amplification. The hydrogels can encapsulate bioactive agents for drug delivery.

28 Claims, 8 Drawing Sheets

(56) References Cited

U.S. PATENT DOCUMENTS

2009/0209436 A1      8/2009    Larman et al.
2010/0256017 A1*   10/2010   Larman et al. .................. 506/40
2012/0022244 A1      1/2012    Yin

OTHER PUBLICATIONS

Liedl, et al. Controlled trapping and release of quantum dots in a DNA switchable hydrogel. Small. Oct. 2007;3(10):1688-93.

Logan, et al. Adenovirus tripartite leader sequence enhances translation of mRNAs late after infection. Proc Natl Acad Sci U S A. Jun. 1984;81(12):3655-9.

Pearson, et al. Improved tools for biological sequence comparison. Procs. Natl. Acad. Sci. USA. 1988; 85:2444-2448.

Scahill, et al. Expression and characterization of the product of a human immune interferon cDNA gene in Chinese hamster ovary cells. Proc Natl Acad Sci U S A. Aug. 1983;80(15):4654-8.

Subramini, et al. Expression of the mouse dihydrofolate reductase complementary deoxyribonucleic acid in simian virus 40 vectors. Mol. Cell. Biol. 1981; 1:854-864.

Urlaub, et al. Isolation of Chinese hamster cell mutants deficient in dihydrofolate reductase activity. Proc Natl Acad Sci U S A. 1980; 77:4216-4220.

Gothelf. Materials science. LEGO-like DNA structures. Science. Nov. 30, 2012;338(6111):1159-60. doi: 10.1126/science.1229960.

Lee, et al. Molecularly self-assembled nucleic acid nanoparticles for targeted in vivo siRNA delivery. Nat Nanotechnol. Jun. 3, 2012;7(6):389-93. doi: 10.1038/nnano.2012.73.

Li, et al. Self-assembled multivalent DNA nanostructures for noninvasive intracellular delivery of immunostimulatory CpG oligonucleotides. ACS Nano. Nov. 22, 2011;5(11):8783-9. doi: 10.1021/nn202774x. Epub Oct. 17, 2011.

\* cited by examiner

NUCLEIC ACID HYDROGEL VIA ROLLING CIRCLE AMPLIFICATION

The application claims the benefit of U.S. Provisional Patent Application No. 61/204,385 to Luo, filed on Jan. 5, 2009, which is entirely incorporated herein by reference.

SEQUENCE LISTING

The instant application contains a Sequence Listing which has been submitted via EFS-Web and is hereby incorporated by reference in its entirety, Said ASCII copy, created on Mar. 23, 2010, is named 32497718.txt and is 1,311bytes in size.

BACKGROUND OF THE INVENTION

Nucleic acid hydrogels have been useful for numerous applications including tissue engineering, drug delivery and diagnosis. Previous methods for forming hydrogels can depend on the base pairing of nucleic acids and covalent crosslinking, e.g., ligation with T4 ligase. These processes are complicated for some applications. The invention provides processes for creating nucleic acid based gels without crosslinking to provide flexibility in design and fabrication. Furthermore, the gels provided by the invention have properties that are not achieved through other routes of formation.

SUMMARY OF THE INVENTION

In embodiments of the invention, methods for forming hydrogels are provided that do not rely on the chemical crosslinking of branched nucleic acids (e.g., DNA) for the formation of a nucleic acid-containing hydrogels.

In various embodiments, the construction of nucleic acid hydrogel is described via elongation by rolling circle amplification (RCA). In an embodiment, this process is based on the physical interaction(s) of long single stranded nucleic acid polymers, e.g., via entanglement as opposed to association primarily through covalent crosslinking. These nucleic acid hydrogels are biocompatible and biodegradable and can be almost fluidic-like while retaining gel properties. Nucleic acid hydrogels formed according to methods of the invention can be transformed between desirable shapes depending on the mold.

In one aspect, the invention provides a nucleic acid-containing hydrogel comprising entangled single-stranded nucleic acid molecules, wherein at least a portion of the single-stranded entangled nucleic acid molecules are formed via rolling cycle amplification.

In another aspect, the invention provides a method for forming a nucleic acid-containing hydrogel, comprising entangling single-stranded nucleic acid molecules, wherein at least a portion of the single-stranded nucleic acid molecules are formed by amplifying a circular nucleic acid template.

In embodiments of the hydrogels of the invention, the nucleic acid molecules comprise deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA). For example, the first and second single-stranded nucleic acid molecules can comprise these substituents. Similarly, the circular nucleic acid template may comprise deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA). In embodiments of the invention, the circular nucleic acid template and/or amplification products are amplified with Φ29 DNA polymerase.

In another aspect, the invention provides a method for forming a hydrogel, comprising entangling one or more of a first single-stranded nucleic acid molecule and a second single-stranded nucleic acid molecule, wherein the first single-stranded nucleic acid molecule is formed by amplifying a circular nucleic acid template.

In some embodiments, the first single-stranded nucleic acid molecule is formed by amplifying a circular nucleic acid template using a first primer. The first primer can be complementary to a portion of the circular nucleic acid template.

In some embodiments, the second single-stranded nucleic acid molecule is formed by amplifying the first single-stranded nucleic acid molecule using a second primer. The second primer can be complementary to a portion of the first single-stranded nucleic acid product. In some embodiments, the second primer is complementary to the first primer.

In some embodiments, the method further comprises entangling a third single-stranded nucleic acid molecule with one or more of the first and second single-stranded nucleic acid molecules. The third single-stranded nucleic acid molecule can be formed by amplifying the second single-stranded nucleic acid molecule using a third primer. The third primer can be complementary to a portion of the second single-stranded nucleic acid molecule.

In some embodiments, the hydrogel is formed by entangling the first single stranded nucleic acid molecule with the second single-stranded nucleic acid molecule.

In some embodiments, the circular nucleic acid template is amplified with Φ29 DNA polymerase. The circular nucleic acid template can be amplified by nicking.

In another aspect, the present invention provides a nucleic acid-containing hydrogel, comprising: a first single-stranded nucleic acid molecule, the first single-stranded nucleic acid molecule formed from the amplification of a circular nucleic acid template using a first primer; and a second single-stranded nucleic acid molecule, the second single-stranded nucleic acid molecule formed from the amplification of the first single-stranded nucleic acid molecule using a second primer.

In some embodiments, the method further comprises a third single-stranded nucleic acid molecule, the third single-stranded nucleic acid molecule formed from the amplification of the second single-stranded nucleic acid molecule using a third primer. In some embodiments, the third primer is complementary to a portion of the circular nucleic acid template. In some embodiments, the third primer is complementary to a portion of the second single-stranded nucleic acid molecule. In some embodiments, the third single-stranded nucleic acid molecule is entangled with one or both of the first single-stranded nucleic acid molecule and the second single-stranded nucleic acid molecule.

In some embodiments, the first primer is complementary to a portion of the circular nucleic acid template. In some embodiments, the first primer is complementary to the second primer. In some embodiments, the second primer is complementary to a portion of the first single-stranded nucleic acid molecule. In some embodiments, the second single-stranded nucleic acid molecule is entangled with the first single-stranded nucleic acid molecule.

One or both of the first and second single-stranded nucleic acid molecules can comprise deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA).

In another aspect, the present invention provides a nucleic acid-containing hydrogel, comprising: a first single-stranded nucleic acid molecule, the first single-stranded nucleic acid molecule formed from the amplification of a circular nucleic acid template using a first primer; and a second nucleic acid molecule.

In some embodiments, the second nucleic acid molecule is single-stranded. In some embodiments, the second nucleic acid molecule is double-stranded. In an exemplary embodiment, the first nucleic acid molecule comprises DNA and the second nucleic acid molecule comprises RNA.

In an aspect, the invention provides a method for forming a hydrogel, comprising: hybridizing a circular nucleic acid template with a first primer; forming a first nucleic acid molecule from the first primer; hybridizing a second primer with the first single-stranded nucleic acid molecule; and forming a second nucleic acid molecule from the second primer.

In some embodiments, the method further comprises hybridizing a third primer with the second single-stranded nucleic acid molecule and forming a third nucleic acid molecule from the third primer.

In some embodiments, the method further comprises entangling one or more of the first nucleic acid molecule and the second nucleic acid molecule to form the hydrogel. In some embodiments, the method further comprises entangling the first nucleic acid molecule prior to forming the second nucleic acid molecule.

In some embodiments, the second nucleic acid molecule is at least partially complementary to the first nucleic acid molecule. In some embodiments, the third nucleic acid molecule is at least partially complementary to the second nucleic acid molecule. In some embodiments, the nucleic acid molecules comprise single-stranded nucleic acid molecules.

In another aspect, the invention provides a method of encapsulating one or more compounds in a nucleic acid hydrogel, comprising the steps of: a) providing an aqueous solution comprising said one or more compounds; b) mixing said aqueous solution with a mixture comprising a plurality of circular nucleic acid templates; and c) amplifying the circular nucleic acid template to form the hydrogel, thereby encapsulating the one or more compounds in the hydrogel.

In some embodiments, the one or more compound comprises a biologically active agent, e.g., a drug. In some embodiments, the one or more compound comprises a cell. The cell can be a mammalian cell. In some embodiments, the one or more compound comprises the cell and a virus. In some embodiments, the one or more compound comprises the cell and a biologically active agent. In some embodiments, the one or more compound comprises the cell, a biologically active agent and a virus.

In another aspect, the invention provides a method for delivering a compound, comprising: providing a composition comprising single-stranded nucleic acid molecules encapsulating the compound, wherein at least a portion of the single-stranded nucleic acid molecules are formed by rolling circle amplification; and administering the composition to a subject.

In some embodiments, the compound comprises a biologically active agent. In some embodiments, the compound comprises a cell. In some embodiments, administering the composition to the subject comprises delivering the compound to a cell, tissue, organ, or skin of the subject. In some embodiments, the compound is delivered in a time controlled manner.

In another aspect, the invention provides a method of cell-free synthesis of one or more proteins, comprising: a) providing a composition comprising single-stranded nucleic acid molecules, wherein at least a portion of the single-stranded nucleic acid molecules are formed by rolling circle amplification; and b) expressing the one or more proteins from the nucleic acid hydrogel.

In some embodiments, the hydrogel comprises coding and non-coding nucleic acid molecules. In some embodiments, the hydrogel comprises one or more macromolecules necessary for protein modification, thus producing modified proteins. In some embodiments, the modifications comprise one or more of phosphorylation, glycosylation, methylation, ubiquitination, biotinylation, alkylation, acetylation, glutamylation, glycylation, isoprenylation, lipoylation, phosphoantetheinylation, sulfation, citrullination, deamidation, or isomerization.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2a shows a swollen DNA hydrogel in water, in accordance with an embodiment of the invention. FIGS. 2b and 2c show DNA hydrogels stained with GelGreen, DNA-specific fluorescent dyes, in accordance with an embodiment of the invention. The scale bar is 10 mm.

FIG. 3a is a profile of a first gelation process (gelation 1) with three different conditions using 10 nM circular RCA templates and 1 unit/$\mu$L of $\Phi$29 DNA polymerase (♦), 2 nM circular RCA templates and 1 unit/$\mu$L of $\Phi$29 DNA polymerase (●), and 10 nM circular RCA templates and 0.2 unit/$\mu$L of $\Phi$29 DNA polymerase (▲), in accordance with an embodiment of the invention. FIG. 3b is a profile of a second gelation process (gelation 2) by adding 10 pM of primer 2 and primer 3 after gelation 1 of the conditions with 10 nM circular RCA templates and 1 unit/$\mu$L of $\Phi$29 DNA polymerase (♦), in accordance with an embodiment of the invention;

DETAILED DESCRIPTION OF THE INVENTION

Figure 1:
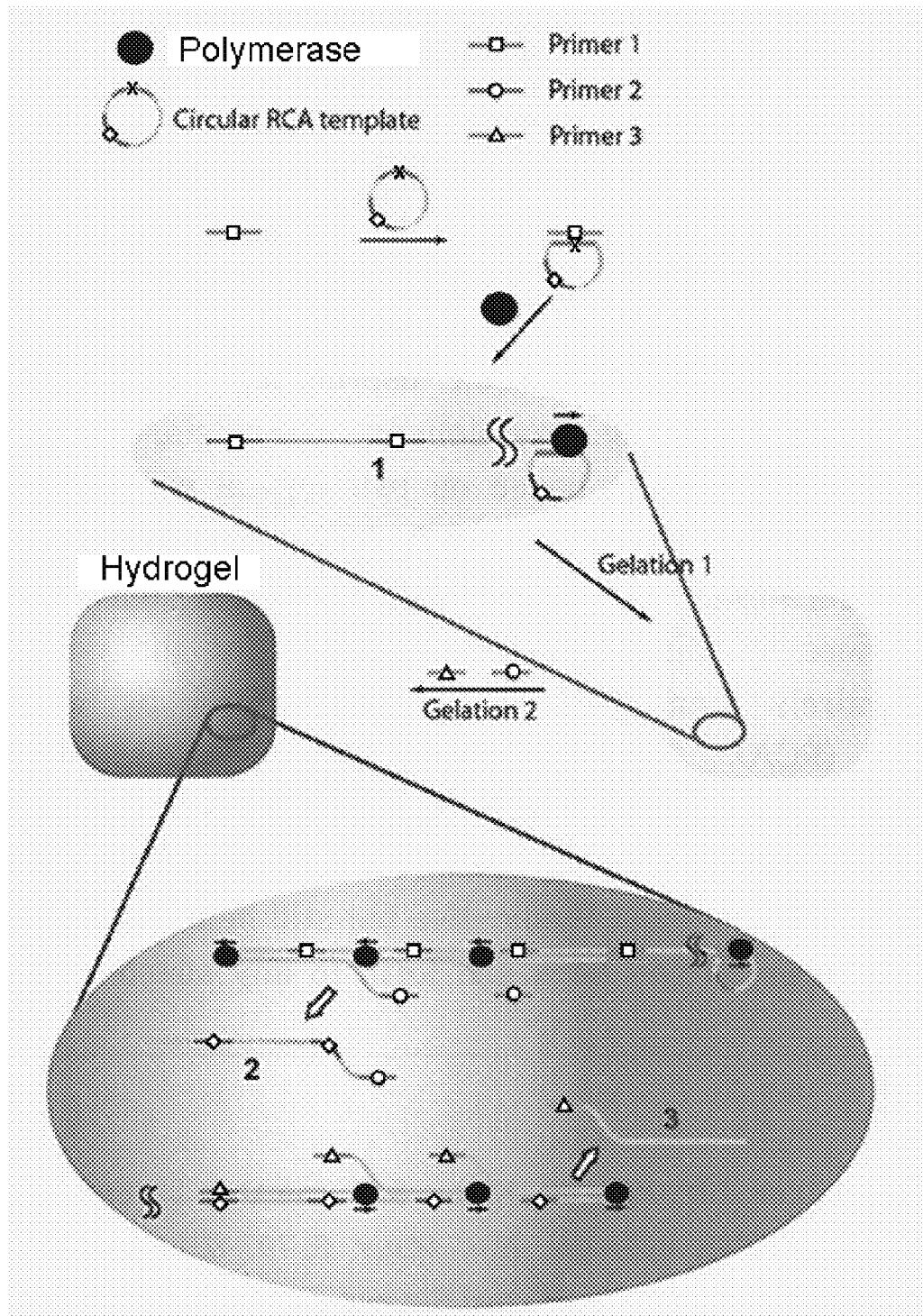
FIG. 1 schematically illustrates a rolling circle amplification process, in accordance with an embodiment of the invention.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural and logical changes can be made without departing from the scope of the present invention. The following description of example embodiments is, therefore, not to be taken in a limited sense, and the scope of the present invention is defined by the appended claims.

Nucleic acid hydrogels can be used for numerous applications, including tissue engineering, drug delivery and diagnosis. Hydrogels can be formed from nucleic acids in various ways. For example, hydrogels can be formed from the enzyme-catalyzed assembly of synthetic branched DNA. See Um, S. H., Lee, J. B., Park, N., Kwon, S. Y., and Dan. L., Enzyme catalyzed assembly of DNA hydrogel, *Nat. Mater.* 5, 797 801 (2006); U.S. patent application Ser. No. 11/464,181 ("NUCLEIC ACID-BASED MATRIXES") to Luo et al.; U.S. patent application Ser. No. 11/464,184 ("NUCLEIC ACID-BASED MATRIXES FOR PROTEIN PRODUCTION") to Luo et al.; U.S. patent application Ser. No. 11/423,633 ("DETECTION OF TARGET MOLECULES WITH LABELED NUCLEIC ACID DETECTION MOLECULES") to Luo et al.; and PCT Patent Application PCT/US2009/52795, filed Aug. 5, 2009 and entitled "PHOTO-CROSSLINKING-BASED METHOD FOR CREATING DNA HYDROGELS," each of which are incorporated herein by reference in their entirety. As another example, hydrogels can be formed by DNA polymer conjugation in a semi interpenetrating network (semi IPN) manner. See Liedl, T., Dietz, H., Yurke, B., and Simmel, F., Controlled Trapping and Release of Quantum Dots in a DNA-Switchable Hydrogel, *Small* 3, 1688-1693 (2007), which is entirely incorporated herein by reference.

In embodiments of the invention, hydrogels are formed from a nucleic acid (e.g., DNA, RNA) that is elongated by rolling circle amplification (RCA). This gelling process is based on physical interactions of long nucleic acid strands instead of crosslinking. These nucleic acid (also "nucleic acid-containing" herein) hydrogels, which are biocompatible and biodegradable, can be almost fluidic-like although exhibiting gel properties. Hydrogels formed according to methods of embodiments of the invention can be between desirable shapes depending on the mold.

The practice of various embodiments of the invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform various functions, known or unknown. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), complementary DNA (cDNA), recombinant polynucleotides, branched polynucleotides, plasmids, vectors, isolated DNA (A, B and Z structures) of any sequence, peptide nucleic acid (PNA), locked nucleic acid (LNA), threose nucleic acid (TNA), glycol nucleic acid (GNA), isolated RNA of any sequence, nucleic acid probes, and primers. Small interfering RNA (siRNA), sometimes known as short interfering RNA or silencing RNA, are typically double-stranded RNA molecules of about 15-35 nucleotides in length. siRNA can interfere with the expression of certain genes. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability. miRNAs are single-stranded RNA molecules of 21-23 nucleotides in length. miRNAs are typically partially complementary to one or more messenger RNA (mRNA) molecules, and hybridize thereto to down-regulate gene expression. Small nuclear RNA (snRNA) is a class of small RNA molecules that are found within the nucleus of eukaryotic cells. snRNA are involved in a variety of biological processes such as RNA splicing, regulation of transcription factors (7SK RNA) or RNA polymerase II (B2 RNA), and maintaining telomeres. They associate with specific proteins, and the complexes are referred to as small nuclear ribonucleoproteins (snRNP) or "snurps." GNA's comprises repeating glycerol units linked by phosphodiester bonds, and TNA's backbone comprises repeating threose units linked by phosphodiester bonds.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components.

A primer can include a nucleic acid with a free 3' hydroxyl end that can serve an initiation site for DNA synthesis, e.g., by DNA polymerase III. A primer can comprise a short oligonucleotide. Non-specific priming can be performed with shorter nucleic acids with less specific binding, e.g., having a length of about 5, 6, 7, 8, 9, 10, 11, 12, 13, 14, 15, 16 base pairs. Oligonucleotide primers are typically about 15 to 100 base pairs, e.g., about 18-50 base pairs, or about 20-25 base pairs in length. Longer nucleic acids can also serve as primers within the scope of the invention, e.g., an entire strand of a double stranded circular template can serve as a primer as a nick site.

A polynucleotide may be further modified after polymerization, such as by conjugation with a labeling component. The nucleic acids, used in the various embodiments disclosed herein, may be modified in a variety of ways, including by crosslinking, intra-chain modifications such as methylation and capping, and by copolymerization. Additionally, other beneficial molecules may be attached to the nucleic acid chains. For example, photo-crosslinkable moieties can be attached to the nucleic acid chains. The nucleic acids may have naturally occurring sequences or artificial sequences. The sequence of the nucleic acid may be irrelevant for many aspects disclosed herein. However, special sequences may be used to prevent significant effects due to the information coding properties of nucleic acids, to elicit particular cellular responses or to govern the physical structure of the molecule.

As used herein, nucleic acid "entanglement" can refer to one or more nucleic acid molecules having segments in proximity to one another such that the segments interact with one another without relying primarily on base pairing between complementary strands. In certain embodiments, the entangled nucleic acid segments can interlock or cross one another. This can occur through hydrophobic interactions, hydrogen bonding, ionic bonding, and/or dipole-dipole interactions between the segments. Entangled nucleic acids can be primarily single-stranded as opposed to base paired. In some embodiments, entangled nucleic acids comprise at least about 10%, 20%, 30%, 40%, 50%, 60%, 70%, 80%, 90%, or at least about 95% single-stranded nucleic acid. The remainder of the nucleic acids can comprise base paired or double-stranded molecules. The single-stranded nucleic acids can be interlocked or interwoven as described herein.

As used herein, a "hydrogel" can include material comprising single or double-stranded nucleic acids. For example, a hydrogel can include entangled single-stranded nucleic acids (e.g., single-stranded DNA). Nucleic acid hydrogels made from branched chain nucleic acid structures have been described in U.S. patent application Ser. No. 11/464,181 ("NUCLEIC ACID-BASED MATRIXES") to Luo et al., U.S. patent application Ser. No. 11/464,184 ("NUCLEIC ACID-BASED MATRIXES FOR PROTEIN PRODUCTION") to Luo et al., U.S. patent application Ser. No. 11/423,633 ("DETECTION OF TARGET MOLECULES WITH LABELED NUCLEIC ACID DETECTION MOLECULES") to Luo et al., and PCT Patent Application PCT/US2009/52795, filed Aug. 5, 2009 and entitled "PHOTO-CROSSLINKING-BASED METHOD FOR CREATING DNA HYDROGELS," each of which are incorporated herein by reference in its entirety.

In some embodiments, the hydrogels provided herein can be used to encapsulate biologically active agents. As used herein, the terms "biologically active agent" and "bioactive agent" can be used interchangeably and include but are not limited to a biological or chemical compound, such as, e.g., a simple or complex organic or inorganic molecule, peptide, peptide mimetic, protein (e.g. antibody, angiogenic, anti-angiogenic and cellular growth factors), an antigen or immunogen, liposome, small interfering RNA (siRNA), or a polynucleotide (e.g. vector, virus, viral vector, or anti-sense), therapeutic agents, organic or inorganic molecules can include a homogenous or heterogeneous mixture of compounds, including pharmaceuticals, radioisotopes, crude or purified plant extracts, and/or a cell, entities that alter, inhibit, activate, or otherwise affect biological or biochemical events, including classes of molecules (e.g., proteins, amino acids, peptides, polynucleotides, nucleotides, carbohydrates, sugars, lipids, nucleoproteins, glycoproteins, lipoproteins, steroids, growth factors, chemoattractants, aptamers, etc.) that are commonly found in cells and tissues, whether the molecules themselves are naturally-occurring or artificially created (e.g., by synthetic or recombinant methods). Such agents may be naturally derived or synthetic. "Therapeutic agents" include molecules or atoms which are useful for therapy. Examples of therapeutic agents include without limitation drugs, toxins, immunomodulators, chelators, antibodies, antibody-drug conjugates, photoactive agents or dyes, and radioisotopes.

Examples of such agents include but are not limited to drugs, for example, small molecules, anti-cancer substances, analgesics, opioids, anti-AIDS substances, anti-cancer substances, immunosuppressants (e.g., cyclosporine), anti-viral agents, enzyme inhibitors, neurotoxins, hypnotics, anti-histamines, lubricants, tranquilizers, anti-convulsants, muscle relaxants and anti-Parkinson agents, anti-spasmodics and muscle contractants including channel blockers, miotics and anti-cholinergics, anti-glaucoma compounds, anti-parasite, anti-protozoal, and/or anti-fungal compounds, modulators of cell-extracellular matrix interactions including cell growth inhibitors and anti-adhesion molecules, vasodilating agents, inhibitors of DNA, RNA or protein synthesis, anti-hypertensives, anti-pyretics, steroidal and non-steroidal anti-inflammatory agents, anti-angiogenic factors, anti-secretory factors, anticoagulants and/or antithrombotic agents, local anesthetics, ophthalmics, prostaglandins, targeting agents, neurotransmitters, proteins, cell response modifiers, and vaccines.

In some embodiments, a drug for use with the invention has been deemed safe and effective for use by the appropriate governmental agency or body. For example, drugs for human use listed by the United States Food and Drug Administration (FDA) under 21 C.F.R. §§330.5, 331 through 361, and 440 through 460; drugs for veterinary use listed by the FDA under 21 C.F.R. §§500 through 589, which are incorporated herein by reference. Such agents are contemplated for use in accordance with compositions and methods disclosed herein.

In some embodiments, at least a portion of the nucleic acid molecules used with the invention is linked to one or more additional compounds, e.g., compounds comprising functional moieties. Non-limiting examples of the one or more additional compounds include a peptide, a polypeptide, a protein, a lipid, a carbohydrate, an aptamer, an antibody, an antigen, a cell growth factor, a DNA binding agent, a detectable label, a selectable marker, biotin, a pharmaceutical agent, a drug, a small molecule, a therapeutic agent, a receptor molecule, a ligand, a nucleic acid molecule or a substrate. In some embodiments, the other biological molecules are also photo-crosslinked to the nucleic acids. The nucleic acids can also be linked, e.g., via photo-crosslinks, with one or more polymers.

Non-limiting examples of useful polymers include poly (ethylene glycol) (PEG), poly(N-isopropylacrylamide), poly (N-alkylacrylamide), poly(N-n-propylacrylamide), poly(N-isopropylmethacrylamide), a peptide, a polypeptide, poly (ethylene oxide)-poly(propylene oxide)-poly(ethylene oxide), poly(DTEC), dextran-polylactide, elastin-like polypeptides, a polyester, polylactide, poly(L-lactic acid), poly(D,L-lactic acid), poly(lactide-co-glycolides), biotinylated poly(ethylene glycol-block-lactic acid), poly(alkylcyanoacrylate), poly(epsilon-caprolactone), polyanhydride, poly(bis(p-carboxyphenoxy) propane-sebacic acid), polyorthoester, polyphosphoester, polyphosphazene, polystyrene, polyurethane, poly(amino acid), poly(ethylene oxide), poly(ethylene oxide)-polypropylene-poly(ethylene oxide), poly(lactic acid)-g-poly(vinyl alcohol), poly(ethylene oxide)-poly(L-lactic acid), poly(D,L-lactic-co-glycolic acid)-poly(ethylene glycol), poly(L-lactide-ethylene glycol), poly(ethylene glycol)-co-poly(hydroxyl Acid), poly(vinyl alcohol), poly(lactic acid-co-lysine)-poly(aspartic acid), poly (-caprolactone-co-trimethylene carbonate), poly(L-lactic acid-co-glycolic acid-co-L-serine), poly(propylene fumarate), oligo(poly(ethylene glycol) fumarate), poly(propylene furmarate-co-ethylene glycol), poly(ethylene glycol) di[ethylphosphatidyl(ethylene glycol)methacrylate], poly(N-isopropylacrylamide)-poly(ethylene glycol), poly(N-isopropylacrylamide)-gelatin, poly(N-isopropylacrylamide-acrylic acid) or a derivative of any thereof.

In some embodiments of the invention, the nucleic acids are linked to a detectable label. Detectable labels for use with the invention include a radiolabeled probe, a fluorophore-labeled probe, a quantum dot-labeled probe, a chromophore-labeled probe, an enzyme-labeled probe, an affinity ligand-labeled probe, an electromagnetic spin labeled probe, a heavy atom labeled probe, or a nanoparticle light scattering labeled probe. In some embodiments, the detectable label comprises a chromophore, a fluorescent moiety, an enzyme, an antigen, a heavy metal, a magnetic probe, a dye, a nanocrystal, a phosphorescent group, a radioactive material, a chemiluminescent moiety, a scattering nanoparticle, a fluorescent nanoparticle, a Raman signal generating moiety, or an electrochemical detection moiety. In some embodiments, the detectable label comprises horseradish peroxidase, alkaline phosphatase, β-galactosidase, acetylcholinesterase, streptavidin, avidin, biotin, an aptamer, an antigen, an antibody, an immunoglobulin, an anti-immunoglobulin, umbelliferone, fluorescein, fluorescein isothiocyanate (FITC), rhodamine, tetramethyl rhodamine, TRITC, eosin, green fluorescent protein, erythrosin, coumarin, methyl coumarin, pyrene, malachite green, stilbene, lucifer yellow, Cascade Blue™, Texas Red, Phar-Red, allophycocyanin (APC), dichlorotriaziny-lamine fluorescein, dansyl chloride, R-phycoerythrin, phycoerythrin, a fluorescent lanthanide complex, Europium, Terbium, Cy3, Cy5, Cy7, digoxigenin, dinitrophenyl, a molecular beacon, a fluorescent molecular beacon derivative, luminol, a light scattering material, a plasmon resonant material, gold, silver, a quantum dot, $^{14}C$, $^{123}I$, $^{124}I$, $^{125}I$, $^{131}I$, Technetium-99 m ($^{Tc}99$ m), $^{35}S$, $^{32}P$ or $^{3}H$. The detectable label can be used as a tracer.

The primers of the invention can be configured to bind specifically or non-specifically to the vectors that are amplified. One of skill will appreciate that the primers can thus be designed for more stringent and more specific binding or less stringent and less specific binding. The following terms can be used to describe the sequence relationships between two or more polynucleotides: (a) "reference sequence," (b) "comparison window," (c) "sequence identity," (d) "percentage of sequence identity," and (e) "substantial identity."

As used herein, "reference sequence" can be a defined sequence used as a basis for sequence comparison. A reference sequence may be a segment of or the entirety of a specified sequence.

As used herein, "comparison window" can make reference to a contiguous and specified segment of a polynucleotide sequence, wherein the polynucleotide sequence in the comparison window may include additions or deletions (i.e., gaps) compared to the reference sequence (which does not include additions or deletions) for optimal alignment of the two sequences. Generally, the comparison window is at least 5, 10, or 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty can be introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, *CABIOS*, 4:11 (1988), which is hereby incorporated by reference in its entirety; the local homology algorithm of Smith et al., *Adv. Appl. Math.*, 2:482 (1981), which is hereby incorporated by reference in its entirety; the homology alignment algorithm of Needleman and Wunsch, *JMB*, 48:443 (1970), which is hereby incorporated by reference in its entirety; the search-for-similarity-method of Pearson and Lipman, *Proc. Natl. Acad. Sci. USA*, 85:2444 (1988), which is hereby incorporated by reference in its entirety; the algorithm of Karlin and Altschul, *Proc. Natl. Acad. Sci. USA*, 87:2264 (1990), which is hereby incorporated by reference in its entirety; modified as in Karhn and Altschul, *Proc. Natl. Acad. Sci. USA*, 90:5873 (1993), which is hereby incorporated by reference in its entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al., *Gene*, 73:237 (1988), Higgins et al., *CABIOS*, 5:151 (1989); Corpet et al., *Nucl. Acids Res.*, 16:10881 (1988); Huang et al., *CABIOS*, 8:155 (1992); and Pearson et al., *Meth. Mol. Biol.*, 24:307 (1994), which are hereby incorporated by reference in their entirety. The ALIGN program is based on the algorithm of Myers and Miller, supra. The BLAST programs of Altschul et al., *JMB*, 215:403 (1990); *Nucl. Acids Res.*, 25:3389 (1990), which are hereby incorporated by reference in their entirety, are based on the algorithm of Karlin and Altschul supra.

Software for performing BLAST analyses is publicly available through the National Center for Biotechnology Information (worldwideweb.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues, always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al., *Nucleic Acids Res.* 25:3389 (1997), which is hereby incorporated by reference in its entirety. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See worldwideweb.ncbi.nlm.nih.gov. Alignment may also be performed manually by inspection.

Comparison of nucleotide sequences for determination of percent sequence identity to the sequences disclosed herein can be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

As used herein, "sequence identity" or "identity" in the context of two nucleic acid sequences can make reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and, therefore, do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" can refer to the value determined by comparing two optimally aligned sequences over a comparison window, wherein the portion of the polynucleotide sequence in the comparison window may include additions or deletions (i.e., gaps) as compared to the reference sequence (which does not include additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide includes a sequence that has at least 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

The term "hybridized" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

As is known to one skilled in the art, hybridization can be performed under conditions of varying stringency. Suitable hybridization conditions are such that the recognition interaction between the probe and target ER-stress related gene is both sufficiently specific and sufficiently stable. Conditions that increase the stringency of a hybridization reaction are widely known and published in the art. See, for example, (Sambrook, et al., (1989), supra; Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferable hybridization assay is conducted on high-density gene chips as described, for example, in U.S. Pat. No. 5,445,934, which is entirely incorporated herein by reference.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution.

For DNA-DNA hybrids, the $T_m$ can be approximated from the equation of Meinkoth and Wahl, *Anal. Biochem.*, 138:267 (1984), which is hereby incorporated by reference in its entirety; $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH.

However, severely stringent conditions can use a hybridization and/or wash at 1, 2, 3, or 4° C. lower than the thermal melting point ($T_m$); moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, *Laboratory Techniques in Biochemistry and Molecular Biology Hybridization with Nucleic Acid Probes*, Part I Chapter 2 "Overview of Principles of Hybridization and the Strategy of Nucleic Acid Probe Assays," Elsevier, N.Y. (1993), which is hereby incorporated by reference in its entirety. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook above for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g. more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Nucleic Acid-Containing Hydrogels

In an aspect of the invention, a method for forming a nucleic acid-containing hydrogel comprises entangling single-stranded nucleic acid molecules. In an embodiment, at least a portion of the single-stranded nucleic acid molecules are formed by amplifying a circular nucleic acid template. In an embodiment, the circular nucleic acid template is amplified through rolling circle amplification ("RCA").

In embodiments, single-stranded nucleic acid molecules are formed via one or more gelation steps. The term "gelation," as used herein, can refer to a process that includes solidification by cooling, a chemical reaction and/or interaction between nucleic acid molecules. During solidification, the viscosity of a solution comprising nucleic acids can increase. During gelation, a gel-like composition can form, e.g., a hydrogel can form during gelation. Hydrogels can comprise a network of polymer chains that are water-insoluble, sometimes found as a colloidal gel in which water is the dispersion medium. Hydrogels can be highly absorbent natural or synthetic polymers. Nucleic acid hydrogels comprise nucleic acid monomers. In some embodiments, hydrogels can contain over more than about 10%, 20%, 30%, 40%, 50%, 51%, 52%, 53%, 54%, 55%, 56%, 57%, 58%, 59%, 60%, 61%, 62%, 63%, 64%, 65%, 66%, 67%, 68%, or 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% water. Hydrogels may possess a degree of flexibility very similar to natural tissue, due to their significant water content. In an embodiment, the hydrogels of the invention can form, at least in part, via entanglement between nucleic acid molecules. The entangled nucleic acids can be single-stranded or double-stranded.

In embodiments, a first single-stranded nucleic acid molecule is formed by RCA. In an embodiment, the first single-stranded nucleic acid molecule is formed with the aid of a first primer and a nucleic acid polymerase. In some embodiments, a second single-stranded nucleic acid molecule is formed by amplifying the first single-stranded nucleic acid with the aid of a second primer and a polymerase (e.g., Φ29 DNA polymerase). In an embodiment, a third single-stranded nucleic acid molecule is formed by amplifying the second single-stranded nucleic acid molecule with the aid of a third primer and a polymerase.

The above process can be repeated with as many primers as desired, e.g., 4, 5, 6, 7, 8, 9, 10 or more primers can be used. In some embodiments, a plurality of primers can be added to template DNA to form a nucleic acid hydrogel, wherein the plurality can comprise at least about 2, 3, 4, 5, 6, 7, 8, 9, 10, 15, 20, 25, 30, 35, 40, 45, 50, 55, 60, 65, 70, 75, 80, 85, 90, 95, or 100 primers. In some embodiments, more than 100 primers are used. In some embodiments, random fragments of short nucleic acid fragments, e.g., comprising digested or otherwise degraded DNAs, are used as non-specific primers to prime the formation of nucleic acid hydrogels using rolling circle amplification. As described herein and will be appreciated by those of skill in the art, the polymerization reaction conditions can be adjusted as desired to form the subject hydrogels. For example, reaction conditions that favor stringent nucleic acid hybridization, e.g., high temperature, can be used to favor more specific primer binding during hydrogel formation.

Unlike other common amplification procedures, e.g., polymerase chain reaction (PCR), RCA produces a single amplified product that remains linked to the DNA primer. In this form of replication, a single replication fork progresses around a circular molecule to form multiple linear copies of the DNA sequence. Because there is no termination point, synthesis often continues beyond a single circle unit, producing concatamers (a series of linked chains) of multiple circle lengths. Φ29 DNA polymerase is commonly used for RCA because it can perform strand displacement DNA synthesis for long stretches of DNA without dissociating from the template. Its stability may also allow DNA synthesis to continue for many hours. Phi29 DNA polymerase is the replicative polymerase from the *Bacillus subtilis* phage phi29 (Φ29). Other nucleic acid polymerases, e.g., DNA or RNA polymerases, may be used as well, e.g., from related phage.

As described above, first and optionally second, third, etc primers can be used to prime the RCA. In an embodiment, the first primer is complementary to a portion of the circular nucleic acid template. In an embodiment, the second primer is complementary to a portion of the first single-stranded nucleic acid molecule. In an embodiment, the third primer is complementary to a portion of the second single-stranded nucleic acid molecule. In an embodiment, the third primer is complementary to a portion of the circular nucleic acid template. A similar scheme can be carried out for subsequent primers, wherein the additional primers can be complementary to the circular nucleic acid template, to the amplification products of the template, or to any further amplification products.

In an embodiment, the third single-stranded nucleic acid molecule has a sequence that is at least partially similar to a nucleic acid sequence (also "sequence" herein) of the first single-stranded nucleic acid molecule. In an embodiment, the second single-stranded nucleic acid molecule has a sequence that is at least partially complementary to the sequence of the first single-stranded nucleic acid molecule.

In an embodiment, after forming the first single-stranded nucleic acid molecule via RCA, a first gelation step is performed to entangle the first single-stranded nucleic acid molecules. In an embodiment, the first gelation step can include cooling a solution having the first single-stranded nucleic acid molecules. Next, in a second gelation step, the second and third primers are provided to a solution comprising the single-stranded nucleic acid molecules. The second and third single-stranded nucleic acid molecules are then formed with the aid of the second and third primers and nucleic acid polymerase. In an embodiment, one or more of the first, second and third single-stranded nucleic acid molecules are then entangled to form a hydrogel. In an embodiment, the first single-stranded nucleic acid molecule is entangled with the second and/or third single-stranded nucleic acid molecules. In an embodiment, the second single-stranded nucleic acid molecule is entangled with the first and/or third single-stranded nucleic acid molecules. In an embodiment, the third single-stranded nucleic acid molecule is entangled with the first and/or second single-stranded nucleic acid molecules.

In an alternative embodiment, following the first gelation step, in the second gelation step the second primer is added to a solution comprising the first single-stranded nucleic acid molecule. The first single-stranded nucleic acid molecule is amplified to form the second single-stranded nucleic acid molecule. Next, in a third gelation step, the third primer is added to a solution comprising the second single-stranded nucleic acid molecule. The third single-stranded nucleic acid molecule is formed by amplifying the second single-stranded with the aid of the third primer and a nucleic acid polymerase. One or more of the first, second and third single-stranded nucleic acid molecules can then be entangled to form a hydrogel.

In embodiments, one or more gelation steps can be used to form a hydrogel. In embodiments, at least 1, 2, 3, 4, 5, 6, 7, 8, 9, 10, 12, 15, 20, 25, 30, 35, 40, 45 or 50 gelation steps can be used to form a hydrogel. In some embodiments, more than 50 gelation steps are performed. In some embodiments, one or more gelation steps can be used to form a plurality of hydrogels having different nucleic acid molecules.

In an embodiment, a single gelation step is used to form a hydrogel. In such a case, one or more primers (e.g., primer 1, primer 2 and primer 3) are added to a solution having a circular nucleic acid template (e.g., circular DNA). RCA of the circular nucleic acid template with the aid of a primer can form a first single-stranded nucleic acid molecule, which can subsequently be amplified with the aid of another primer to form a second single-stranded nucleic acid molecule. In an embodiment, the one or more of the first and second single-stranded nucleic acid molecules can entangle to form the hydrogel. In an embodiment, a solution having the single-stranded nucleic acid molecules can be cooled to form the hydrogel.

In some embodiments, additional single-stranded nucleic acid molecules are formed by amplifying a single-stranded nucleic acid formed in a previous step. Generally, single-stranded nucleic acid molecule 'n' is formed by amplifying single-stranded nucleic acid molecule n-1, wherein n is a number greater than or equal to 2. In embodiments, 'n' can be 3, 4, 5, 6, 7, 8, 9, 10, 12, 15, 20, 25, 30, 35, 40, 45 or 50 or more. In some embodiments, 'n' can be greater than or equal to 2, or greater than or equal to 3, or greater than or equal to 5, or greater than or equal to 10, or greater than or equal to 20, or greater than or equal to 50, or greater than or equal to 100. The formation of 'n' depends on the number of circular nucleic acid templates and primers are added.

In some embodiments, one or more strands are formed by RCA, as described herein. Thereafter, or between gelation or amplification steps, additional nucleic acid strands, e.g., or different lengths or type of nucleic acid are added to the mixture for incorporation into the hydrogel matrix. As a non-limiting example, the circular nucleic acid template comprises DNA. Alternate DNAs, RNAs, or various forms thereof are added after a round of gelation or amplification. In later rounds of gelation or amplification, the alternate DNAs or RNAs can be amplified specifically or non-specifically, or it may entangle with the DNA without amplification. They may comprise single or double stranded molecules. The invention contemplates various such hybrid gels such as these exemplary embodiments. The hybrid gels can thus be configured to manipulate the properties of the final hydrogel, e.g., elasticity, strength, stability, etc.

In embodiments, a method for forming a hydrogel comprises entangling one or more of a first single-stranded nucleic acid molecule and a second single-stranded nucleic acid molecule, wherein the first single-stranded nucleic acid molecule is formed by amplifying a circular nucleic acid template. In an embodiment, the hydrogel is formed by entangling a third single-stranded nucleic acid molecule with the first and/or second single-stranded nucleic acid molecules.

With reference to FIG. 1, in an embodiment, the preparation of hydrogels (also "gels" herein) by rolling circle amplification is schematically illustrated. Primer 1 (marked by boxes) is hybridized with a circular nucleic acid template (e.g., circular DNA template). In a first step, long single-stranded nucleic acid 1 (e.g., ssDNA) with repeated sequence is then created by a nucleic acid polymerase (e.g., Φ29 DNA polymerase). Because of the flexibility of the long single-stranded nucleic acid, product 1 can entangle, thereby forming a gel state. In such a case, the first step can be referred to as a first gelation step, or gelation 1. In an embodiment, primer 1 is complementary to a portion (marked by x's) of the circular nucleic acid template. Next, primer 2 (marked by circles) and primer 3 (marked by triangles) are added to a solution having product 1. In an embodiment, primer 2 is complementary to the portion of amplified single-stranded nucleic acid 1. In an embodiment, primer 2 can hybridize to the single-stranded nucleic acid 1 after first gelation step. Without additional buffer and nucleic acid polymerase, product 2 can polymerize with the primer 2. Product 2 can then hybridize with primer 3 to polymerize product 3. The final polymerized products can then be entangled to make a gel (also "hydrogel" herein).

In an embodiment, primer 3 (triangles) is complementary to a portion of the circular nucleic acid template (diamonds). In an embodiment, primer 3 is complementary to a portion of product 2. In an embodiment, primer 1 is complementary to a first portion of the circular nucleic acid template and primer 3 is complementary to a second portion of the circular nucleic acid template, and the first portion is different from the second. In an embodiment, primer 1 is complementary to primer 2.

In some embodiments, the circular template is amplified without the use of primers. For example, a double stranded circular template can be nicked and then amplified by RCA. An initiator protein e.g., derived from a bacteriophage DNA, can nick one strand of the double-stranded, circular DNA molecule at a site called the double-strand origin, or DSO. The initiator protein may remain bound to the 5' phosphate end of the nicked strand, and the free 3' hydroxyl end is released to serve as a primer for DNA synthesis. Φ29 DNA polymerase or other DNA or RNA polymerase can be used to drive amplification. Using the nicking method, subsequent rounds of amplification could use primers to direct amplification. In some embodiments, RCA by nicking and primer extension are used simultaneously or sequentially.

Methods of embodiments of the invention can be used to form hydrogels of various shapes and sizes. In an embodiment, the hydrogels are spherical (with circular cross-sections). In another embodiment, the hydrogels are box-like. In yet another embodiment, the hydrogels are triangular. Any desirable shape is possible. The shapes of the hydrogels can be manipulated by forming the hydrogel inside a mold. In some embodiments, a preformed hydrogel is placed inside a mold to alter its shape. The shape can thus be altered from one state to another. As with the shapes, the sizes can be manipulated by constraining the hydrogels in a mold during or after their formation. The shape and size of the mold can be freely designed. For example, the size can range from the μm to the cm scale. In some embodiments, the internal gel network structure (matrix) is in the shape of spheres connected by linear threads. The spheres are typically between about 1 μm and 100 μm, or between about 1 μm and 10 μm, or between about 1 μm and 3 μm. In some embodiments, the hydrogels have diameters between about 1 μm and 100 μm, or between about 1 μm and 50 μm, or between about 1 μm and 10 μm. In some embodiments, the hydrogels have diameters between about 1 μm and 10 μm, or between about 2 μm and 6 μm.

In some embodiments, the hydrogels of the invention retain memory of their shape after deformation. For example, a gel can be created by the methods of the invention in a certain shape using a mold or other object. The gel can then be partially or completely dehydrated. Upon rehydration, the hydrogel can retain its original shape.

Hydrogel Encapsulation and Delivery

In an aspect of the invention, one or more biologically active agents (e.g., drugs) or other materials can be encapsulated within the hydrogels of embodiments of the invention. The hydrogels can be used for delivery thereof, e.g., in a controlled release manner as the agents diffuse out of the hydrogel material. In one embodiment, the hydrogel can deliver cells. The cells can be delivered along with one or more biologically active agents. In another embodiment, the hydrogel can provide a scaffold for three-dimensional cell growth or tissue regeneration, either in vitro or in vivo. In yet another embodiment, a hydrogel providing a platform for cell growth or tissue generation concomitantly delivers one or more biologically active agents contained therein and released therefrom.

In embodiments of the invention, a method for delivering a compound comprises providing a composition comprising single-stranded nucleic acid molecules encapsulating the compound. In an embodiment, at least a portion of the single-stranded nucleic acid molecules are formed by rolling circle amplification. In a preferable embodiment, the composition is configured to release the compound in a time-controlled manner. In an embodiment, the composition is configured to release the compound at a rate between about 5% of the total loading per day and about 50% of the total loading per day. In some embodiments, the composition is configured to release the compound at a rate of less than about 1%, 2%, 3%, 4%, 5%, 6%, 7%, 8%, 9%, 10%, 12%, 15%, 20%, 25%, 30%, 35%, 40%, 50%, 55%, 60%, 65%, 70%, 75%, 80%, 85%, 90%, or 95% of the total loading per day. In embodiments, the composition can be administered to a subject. In an embodiment, administering the composition to the subject comprises delivering the compound to a cell, tissue, organ, or skin of the subject. In some embodiments, the composition is configured to release a spike of the compound upon administration followed by a time-controlled release thereafter.

In an embodiment, the subject is a patient or individual in need of the compound. For example, the subject can be a patient or individual in need of treatment. In an embodiment, the composition can be administered by a physician, the subject, a nurse, a physician's assistant, a family member, a veterinarian, or any other appropriate caretaker.

In an embodiment, the compound can be a biologically active agent. In another embodiment, the compound can be a cell. Combinations of biologically active agents and cells can be encapsulated within a single hydrogel preparation.

In various embodiments, bioactive agents and/or cells are contained in an aqueous, physiologically compatible environment during a time period prior to gelation (i.e., pre-gelling), thus allowing the efficiency of encapsulation of such agents to reach close to 100%.

In embodiments, a bioactive agent is provided to a solution comprising one or more nucleic acid molecules, e.g., one or more circular templates. In a preferable embodiment, at least some of the one or more nucleic acid molecules are formed by amplifying a circular nucleic acid template molecule (via RCA). In an embodiment, the solution is in liquid form (i.e., no gelation has occurred). Next, with the bioactive agent and/or cell in solution, gelation is induced to form hydrogels around the bioactive agent and/or cell. In an embodiment, the hydrogels encapsulate at least a portion of the bioactive agent and/or cell. In an embodiment, the hydrogels encapsulate all or substantially all of the bioactive agent and/or cell.

In an embodiment, a hydrogel can comprise a single bioactive agent. In another embodiment, a hydrogel can comprise a plurality of bioactive agents. In some embodiments, a hydrogel can encapsulate a plurality of bioactive agents of the same type. In another embodiment, a hydrogel can encapsulate a plurality of different types of bioactive agents.

Examples of biologically active agents that can be incorporated into the subject hydrogels include but are not limited to bioactive agents delivered alone or in combination with another compound and/or cell. Nonlimiting examples of bioactive agents include interferon, interleukin, erythropoietin, granulocyte-colony stimulating factor (GCSF), stem cell factor (SCI:), leptin (OB protein), interferon (alpha, beta, gamma), ciprofloxacin, amoxycillin, *lactobacillus*, cefotaxime, levofloxacin, cefipime, mebendazole, ampicillin, *lactobacillus*, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, brain derived neurotrophic factor (BDNF), glial derived neurotrophic factor (GDNF), neurotrophic factor 3 (NT3), fibroblast growth factor (FGF), transforming growth factor (TGF), platelet transforming growth factor, milk growth factor, endothelial growth factors (EGF), endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), bone morphogenetic protein 2 (BMP2), BRAK, C-10, Cardiotrophin 1 (CT1), CCR8, anti-inflammatory: paracetamol, salsalate, diflunisal, mefenamic acid, diclofenac, piroxicam, ketoprofen, dipyrone, acetylsalicylic acid, antimicrobials amoxicillin, ampicillin, cephalosporins, erythromycin, tetracyclines, penicillins, trimethprim-sulfamethoxazole, quniolones, amoxicillin, clavulanatf, azithromycin, clarithromycin, anti-cancer drugs aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, anti-virus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetylsalicylic acid, acetaminophen, analgesic, anti-tumor preparation, anti-cancer preparation, anti-proliferative preparation or pro-apoptotic preparation.

In some aspects the hydrogels of the present invention encapsulate a vector exclusively, or along with cells and/or other biologically active agents disclosed herein. Examples of vectors include adenoviral vectors, adenoviral associated vectors, retroviral vectors, and/or plasmid vectors.

In other aspects of the invention the nucleic acid vectors are deposited in the hydrogel of the invention and are delivered to a target cell or tissue. In other aspects, such vectors can encode a therapeutic protein, antisense mRNA or aptamers. In yet other aspects of the invention, one or more vectors each encoding a different therapeutic capable agent delivered to cells or tissue via the hydrogel of the invention. Therefore, the hydrogel of the invention will controllably release vectors to effectuate gene delivery, such as in gene therapy. Gene delivery may be either endogenously or exogenously controlled. Examples of endogenous control include promoters which are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

In an alternative aspect of the invention, the hydrogels can deliver a small molecule drug, such as those described herein, wherein the hydrogel is used to deliver the vector and the inducible agent (e.g., small molecule drug), the vector alone or some combination thereof.

Vectors include derivatives of SV-40, adenovirus, retrovirus-derived DNA sequences and shuttle vectors derived from combinations of functional mammalian vectors and functional plasmids and phage DNA. Eukaryotic expression vectors are well known, e.g. such as those described by P J Southern and P Berg, J Mol Appl Genet 1:327-341 (1982); Subramini et al., Mol Cell. Biol. 1:854-864 (1981), Kaufmann and Sharp, J Mol. Biol. 159:601-621 (1982); Scahill et al., PNAS USA 80:4654-4659 (1983) and Urlaub and Chasin PNAS USA 77:4216-4220 (1980), which are hereby incorporated by reference. The vector used in one or methods disclosed herein may be a viral vector, preferably a retroviral vector. Replication deficient adenoviruses are preferred. For example, a "single gene vector" in which the structural genes of a retrovirus are replaced by a single gene of interest, under the control of the viral regulatory sequences contained in the long terminal repeat, may be used, e.g. Moloney murine leukemia virus (MoMulV), the Harvey murine sarcoma virus (HaMuSV), murine mammary tumor virus (MuMTV) and the murine myeloproliferative sarcoma virus (MuMPSV), and avian retroviruses such as reticuloendotheliosis virus (Rev) and Rous Sarcoma Virus (RSV), as described by Eglitis and Andersen, BioTechniques 6(7):608-614 (1988), which is hereby incorporated by reference.

Recombinant retroviral vectors into which multiple genes may be introduced may also be used with the matrixes or methods of the invention. As described by Eglitis and Andersen, above, vectors with internal promoters containing a cDNA under the regulation of an independent promoter, e.g. SAX vector derived from N2 vector with a selectable marker (noeR) into which the cDNA for human adenosine deaminase (hADA) has been inserted with its own regulatory sequences, the early promoter from SV40 virus (SV40) may be designed and used in accordance with methods disclosed herein or as known in the art.

In some aspects of the invention, the vectors comprising recombinant nucleic acid molecules are first introduced (e.g., transfected) into cells, which cells are deposited in the matrixes of the invention. For example, the vectors comprising the recombinant nucleic acid molecule are incorporated, i.e. infected, into the BM-MNCs by plating ~5e5 BM-MNCs over vector-producing cells for 18-24 hours, as described by Eglitis and Andersen BioTechniques 6(7):608-614 (1988), which is hereby incorporated by reference, and subsequently said cells are deposited into the reservoir portion of the device.

In some aspects of the invention, the nucleic acid molecule encodes proteins such as growth factors, including but not limited to, VEGF-A, VEGF-C, PlGF, KDR, EGF, HGF, FGF, angiopoietin-1, and cytokines In additional preferred embodiments, the nucleic acid molecule encodes endothelial nitric oxide synthases eNOS and iNOS, G-CSF, GM-CSF, VEGF, aFGF, SCF (c-kit ligand), bFGF, TNF, heme oxygenase, AKT (serine-threonine kinase), HIFα (hypoxia inducible factor), Del-1 (developmental embryonic locus-1), NOS (nitric oxide synthase), BMP's (bone morphogenic proteins), SERCA2a (sarcoplasmic reticulum calcium ATPase), $\beta_2$-adrenergic receptor, SDF-1, MCP-1, other chemokines, interleukins and combinations thereof.

In additional preferred embodiments, the nucleic acid molecule encodes transcription factors for stem cells including without limitation Oct3/4, Sox2, Klf4, and/or C-myc. By introducing combinations of these factors, fibroblasts can be re-programmed into induced pluripotent stem cells (iPS cells). iPS cells are a type of pluripotent stem cell artificially derived from a non-pluripotent cell, e.g., an adult somatic cell, by inducing a "forced" expression of certain genes. By using the forced expression of transcriptional factors, one can manipulate differentiation of stem cells. The generation of iPS cells depends on the genes used for the induction. Oct3/4 and certain members of the Sox gene family (Sox1, Sox2, Sox3, Sox15, Sox18) are transcriptional regulators involved in the induction process and may be useful for induction. Additional genes, including certain members of the Klf family (Klf1, Klf2, Klf4, and Klf5), the Myc family (C-myc, L-myc, and N-myc), Nanog, and LIN28, have been identified to increase the induction efficiency. In some embodiments, the vectors encode one or more of Oct3/4, Sox1, Sox2, Sox3, Sox15, Sox18, Klf1, Klf2, Klf4, Klf5, C-myc, L-myc, N-myc, Nanog and LIN28. One of skill will appreciate that the hydrogels of the invention can incorporate other factors that are useful for controlling iPS cell differentiation.

The pluripotent iPS cells can be differentiated into various cells types. For example, the iPS cells may be differentiated into fully differentiated tissues, e.g., neurons, cardiomyocytes, "embryoid bodies," teratomas, and chimeric or non-chimeric animals. In some embodiments, the matrixes of the invention comprise factors to control the differentiation of iPS cells into fully differentiated tissues.

In additional aspects of the invention, the matrixes of the invention comprise genes which may be delivered in the autologous BM-MNCs using one or more methods disclosed herein include but are not limited to nucleic acid molecules encoding factor VIII/von Willebrand, factor IX and insulin, NO creating genes such as eNOS and iNOS, plaque fighting genes, thrombus, deterrent genes, for example. Therefore, in such an example, the hydrogel matrix of the invention contains cells that secrete the therapeutic agent from the pores of the matrix, wherefrom the therapeutic agent exits from the matrix into the surrounding cells (e.g., in vitro or in vivo). It will be appreciated that the preceding growth factors can also be delivered in the form of synthesized or recombinant proteins.

In mammalian host cells, a number of viral-based expression systems can be used. In cases where an adenovirus is used as an expression vector, the nucleotide sequence of interest (e.g., encoding a therapeutic capable agent) can be ligated to an adenovirus transcription or translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the AQP1 gene product in infected hosts. (See e.g., Logan & Shenk, Proc. Natl. Acad. Sci. USA 8 1:3655-3659 (1984)).

Specific initiation signals can also be required for efficient translation of inserted therapeutic nucleotide sequences. These signals include the ATG initiation codon and adjacent sequences. In cases where an entire therapeutic gene or cDNA, including its own initiation codon and adjacent sequences, is inserted into the appropriate expression vector, no additional translational control signals can be needed. However, in cases where only a portion of the therapeutic coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (See e.g., Bittner et al., Methods in Enzymol, 153:516-544 (1987)).

The subject hydrogels are also applicable to non-therapeutic applications such as cell culturing and tissue engineering, by providing a three-dimensional scaffold and/or delivery of biologically active agents (e.g., small molecule drugs, cell growth factors, angiogenic factors). Thus agents that can be controllably released by embodiments of the invention include therapeutic agents, cell culture agents and tissue engineering agents.

As such one aspect of the invention is directed to hydrogels or methods of use thereof, wherein the hydrogel is used to encapsulate a cell. In one embodiment, the hydrogel can be used to propagate and culture cells in vitro. Further, in vitro applications include tissue generation or regeneration, by utilizing the hydrogel either as a structural scaffold or as both a scaffold and source of growth promoting factors. In another embodiment, the hydrogel is implanted into a target site in a subject. The term "implanted" is used to mean any means of delivery known in the art and is not necessarily limited to invasive procedures (e.g., topical, or skin-based applications).

In one embodiment, the hydrogel is used in a cell culture to release a particular agent in a controlled manner to monitor the effects of such an agent on cells or tissue cultures. For example, the subject hydrogels can be used in a method of screening different agents to determine the mechanisms, by which such compounds induce cell differentiation, e.g., such as in studying effects on stem cells. Methods of using cell and tissue culture are known in the art, such as disclosed in U.S. Pat. Nos. 7,008,634 (using cell growth substrates with tethered cell growth effector molecules); 6,972,195 (culturing potentially regenerative cells and functional tissue organs in vitro); 6,982,168 or 6,962,980 (using cell culture to assay compounds for treating cancer); 6,902,881 (culturing techniques to identify substances that mediate cell differentiation); 6,855,504 (culturing techniques for toxicology screening); or 6,846,625 (identifying validated target drug development using cell culture techniques), the disclosure of each of which is herein incorporated by reference. The hydrogel matrixes of the invention are readily adaptable to such cell culturing techniques as would be evident to one of ordinary skill in the art.

In some aspects of the invention, the hydrogel encapsulates cells and a biologically active agent, whereby the hydrogel provides a scaffold on which cells grow/differentiate, either in vitro or in vivo. Furthermore, the hydrogel nucleic acids can be linked to additional copolymers to provide a substrate surface defining a tissue contacting surface, whereby the surface is disposed with polypeptides or peptides which are cell/tissue growth potentiating. The hydrogel can release biologically active agents that are also cell/tissue growth potentiating, where such polypeptides/peptides include PDGF, EGF, FGF, TGF, NGF, CNTF, GDNF, VEGF and type I collagen peptides, or functionally active fragments and/or combinations thereof.

The nucleic acid hydrogel either, optionally further linked with additional polymers as disclosed herein, may be used for a variety of tissue engineering applications including, inter alia, to increase tissue tensile strength, improve wound healing, speed up wound healing, as templates for tissue formation, to guide tissue formation, to stimulate nerve growth, to improve vascularization in tissues, as a biodegradable adhesive, as device or implant coating, or to improve the function of a tissue or body part.

In some embodiments, the hydrogels may also more specifically be used as sutures, scaffolds and wound dressings. The type of nucleic acid polymer or copolymer used may affect the resulting chemical and physical structure of the polymeric biomaterial.

In an another embodiment, a hydrogel is placed in the or on a wound area, whereby the hydrogel controllably releases a desired therapeutic agent that promotes wound healing, exclusive of or in addition to providing a scaffold for cell regrowth/regeneration necessary for improved or faster healing. For example, the therapeutic agent can comprise cell growth or angiogenic factors, described herein, as one of several potential agents.

It will be appreciated that the hydrogels of the invention can be implanted using methods known in the art, including invasive, surgical, minimally invasive and non-surgical procedures. Depending on the subject, target sites, and agent(s) to be delivered the microfabrication techniques disclosed herein, can be adapted to make the delivery scaffold of the invention of appropriate size and shape. The matrix described herein is suitable for use in various locations in the body. For example, they can be implanted on the surface of the skin, under the skin, or in or near internal tissues or organs. The devices in some embodiments are located in or near a gastrointestinal tract, airway tissue or organ, cardiovascular tissue or organ, or neuronal tissue or organ. Other examples of target sites for implantation include but are not limited to the eye, pancreas, kidney, liver, stomach, muscle, heart, lungs, lymphatic system, thyroid gland, pituitary gland, ovaries, prostate, skin, endocrine glands, ear, breast, urinary tract, brain or any other site in an animal.

In certain embodiments, the hydrogels of the invention can be encased in a nonbiodegradable material, which materials are known in the art. For example, if a subject gel is attached to a temporary implant, the gel can be encased in a nonbiodegradable casing. Suitable materials for casings include but are not limited to poly(dimethylsiloxane), silicone elastomers, polyurethane, poly(tetrafluoroethylene), polyethylene, polysulfone, poly(methyl methacrylate), poly(2-hydroxyethyl methacrylate), polyacrylonitrile, polyamides, polypropylene, poly(vinyl chloride), poly(ethylene-co-(vinyl acetate)), polystyrene, poly(vinyl pyrrolidine), yellow wax, petrolatum cholesterol, stearyl alcohol, white wax, white petrolatum, methylparaben, propylparaben, sodium lauryl sulfate, propylene glycol, glycerogelatins, geling agents such as carbomer 934, cellulose derivatives, natural gums, penetration enhancers such as dimethyl sulfoxide, ethanol propylen glycol, glycerin, urea, glycerogelatins, coloring agents, lactose, stearic acid, starch glycolate, sugar, gelatin, fixed vegetable oils and fats, glycerin, propylene glycol, alcohol, ethyl oleate, isopropyl myristate, dimethyl acetamide, and mixtures or aqueous or oil based dispersions of these.

Selection of implantation sites for the hydrogels are within the skill of one of skill in the art. For example, suitable sites for implantation in the eye include the anterior chamber, posterior chamber, vitreous cavity, suprachoroidal space, subconjunctiva, episcleral, intracorneal, epicorneal and sclera. Suitable sites extrinsic to the vitreous comprise the suprachoroidal space, the pars plana and the like. The suprachoroid is a potential space lying between the inner scleral wall and the apposing choroid. Matrixes implanted in a suprachoroid may deliver drugs to the choroid and to the anatomically apposed retina, depending upon the diffusion of the drug from the implant, the concentration of drug comprised in the implant and the like. Additional methods and procedures for implanting a device of the invention in various tissue/organ sites are known in the art, such as disclosed in U.S. Pat. Nos. 7,013,177; 7,008,667; 7,006,870; 6,965,798; 6,963,771; 6,585,763; 6,572,605; or 6,419,709, the disclosure of each of which is herein incorporated by reference.

In another embodiment the hydrogel provides a means for topical delivery, such as to skin. For example, the hydrogel can be encased in a nondegradable casing (e.g., plastics or bandage or patch) providing an aperture or surface for contacting the target site (i.e., skin or wound thereof). Subsequently, the gel can release in a time controlled manner the desired drug to the target site.

One aspect of the invention is directed to use of the hydrogels in wound healing. In general, the body is able to regenerate injured tissue to produce new tissue having properties similar to the original tissue. For example, small cuts heal without forming permanent scars, and clean fractures in bone are healed by the formation of new bone that binds the two fragments of bone together. However, connective tissue cells and other organ cells are anchorage dependent—they require a scaffold to exhibit normal physiological behavior. Where tissue damage is extensive or large gaps are present, cells migrating into the wound may not find proper anchorage and may produce scar tissue to bridge the gap between healthy tissues at the edges of the wound. Scar tissue does not have the same mechanical and biological properties as the original tissue. For example, scar tissue in skin is not as pliable as the original tissue. Scar tissue in bone is not as strong as uninjured bone and often provides a weak point where it is easier to break the bone again. Some tissues, such as articular cartilage, do not naturally regenerate and healing only proceeds by the formation of scar tissue. In another embodiment, the hydrogels provides a scaffold for wound healing (e.g., burns, cuts, deep tissue trauma), which hydrogel can be encased in a nondegradable or degradable casing, or applied without any such casing, to a selected target site. The hydrogel can concomitantly release a desired drug compound while also providing a scaffold/support for cell growth and tissue (e.g., skin) regeneration.

Other methods for encapsulating a bioactive agent and/or a cell in a hydrogel are provided in U.S. patent application Ser. No. 11/464,181 to Luo et al. and U.S. patent application Ser. No. 11/464,184 to Luo et al., which are entirely incorporated herein by reference. The subject hydrogels can also be used to encapsulate and/or deliver the biologically active agents disclosed therein.

In some embodiments, the hydrogels of the invention are used to probe the topology of an cavity of an object, e.g., an internal cavity within an animal, e.g., a human. Accordingly, the gel can be formed inside the cavity using the methods of the invention. Upon removing water from the hydrogel, the gel can be recovered, e.g., by flow taking advantage of the gel's liquid properties. Due to the memory property or the hydrogels, the original shape and topology of the cavity can be recovered after adding water.

In some embodiments, magnetic particles are encapsulated into the hydrogels of the invention. The particles can be either nano or micro size or a combination thereof. Upon adding an external magnetic field, the hydrogel can be induced to move towards the field, thereby compressing the hydrogel and forcing release the contents of the gels, e.g., biologically active agents or cells as described herein. Such methods can be used to control release, e.g., that of a biologically active agent such as a drug, via a remote control.

In some embodiments, a protein or peptide is conjugated to a nucleic acid of the subject hydrogels. The protein or peptide can be chosen to respond to an external stimulus, e.g., an environmental stimulus. The response includes without a change in conformation and/or catalysis of a reaction. Thus, the hydrogels of the invention can be configured to respond to their surroundings.

Protein Production

In another aspect, a gene sequence encoding a protein or other biologically active molecule (e.g., an RNA) can be incorporated into the subject hydrogels. Accordingly, the hydrogels can be used as a cell-free protein production platform. Similar systems have been described in U.S. patent application Ser. No. 11/464,181 ("NUCLEIC ACID-BASED MATRIXES") to Luo et al., U.S. patent application Ser. No. 11/464,184 ("NUCLEIC ACID-BASED MATRIXES FOR PROTEIN PRODUCTION") to Luo et al., and PCT Patent Application PCT/US2009/52795, filed Aug. 5, 2009 and entitled "PHOTO-CROSSLINKING-BASED METHOD FOR CREATING DNA HYDROGELS," all of which are incorporated herein by reference in their entirety.

In some aspects, the nucleic acid hydrogels are directed to producing proteins in a cell-free system. Such matrixes simplify protein expression, because virtually all proteins, including toxic proteins or even multiple proteins, can be expressed from a protein-producing hydrogel ("P-gel") without requiring living organisms/cells. In addition, mutations of any gene can be studied directly at the protein level without transformation and selection. Further, a cell-free system can provide an easier route to purifying final protein products. Such systems eliminate the need to feed live cells, maintain reactors, and perform post-expression purifications. Protein expression using the hydrogels of the invention can be highly efficient whereas and the cost can be low due to the reusability of both enzymes and P-gels.

In an aspect of the invention, a nucleic acid hydrogel is a P-gel matrix, which can be constructed of two categories of nucleic acid molecules. First, nucleic acids are selected for providing a scaffolding for structural support. In addition, the matrix can comprise nucleic acids that encode one or more proteins of interest. Both components can be encoded into a single or multiple circular templates for RCA amplification. In some embodiments, the components are added separately, e.g., the structural support can be provided by hydrogel material formed by RCA, whereas the nucleic acid comprising coding regions comprises separate molecules encapsulated within hydrogel as described herein.

The one or more proteins can be expressed from the hydrogel. A variety of configurations are possible. For example, the hydrogel can comprise both coding and non-coding nucleic acid molecules, e.g., the scaffolding may comprise non-coding regions. The hydrogel can also comprise one or more nucleic acids or other macromolecules necessary for protein modification, e.g., phosphorylation, glycosylation, methylation, ubiquitination, biotinylation, alkylation, acetylation, glutamylation, glycylation, isoprenylation, lipoylation, phosphoantetheinylation, sulfation, citrullination, deamidation, or isomerization. The proteins produced in these embodiments comprise modified proteins, having one of more of the listed modifications or the like.

In some embodiments, the P-gel matrixes are comprised entirely of DNA or RNA or a combination of RNA and DNA, which combinations can comprise each type of nucleic acid as a building block or protein-encoding nucleic acid. Various macromolecules necessary for protein expression/translation are known in the art, such as rabbit reticulocyte, wheat germ and bacterial extracts. As such the matrix can alternatively provide DNA, RNA or a combination of both, whereby the appropriate macromolecules are selected to provide either "coupled" transcription (of DNA) followed by translation into protein, or translation (of RNA) into protein.

Furthermore, by designing matrixes or P-gels with varying concentrations of building block nucleic acids, protein expressing nucleic acids, as well as different ratios of RNA to DNA encoding a protein, various ranges for protein production can be obtained. In yet another embodiment, said structural support is provided by DNA or PNA. In addition, the coding nucleic acid can comprise DNA, RNA, TNA, PNA or a combination thereof (e.g., any two thereof). In yet another embodiment, the P-gel is comprised entirely of DNA.

In one embodiment, proteins are produced directly from the hydrogel via in vitro transcription coupled with translation (TNT). Post-expression purification can be simplified because the system is cell-free and the major components are expressed proteins. Also, both the gels and the TNT enzymes can be recycled and reused, further reducing costs. Maintenance of cells is no longer needed either.

In another embodiment, the protein yield for the matrix is 7.9 mg per cm3 of the gel. In other embodiments, the yield is about 3, 4, 5, 6, 7, 8, 9, 10, 11, 12, 13, 14, 15, 16, 17, 18, 19, 20, 21, 22, 23, 24 or 25 mg per 1 cm3 of the gel.

In yet another aspect, the hydrogel is molded into a matrix forming a hollow structure with one closed end and one open end, or two closed ends, wherein the structure provides surface area internally and externally from which proteins can be transcribed. The concentration of genes a network format such as in a nucleic acid hydrogel provide higher concentrations of genes that kinetically increase the rate of transcription. In addition, the networked scaffolds of nucleic acids provide anchoring sites for more enzymatic activities and turnovers. Moreover, the hollow tube structure provides a concentrated solution of the necessary macromolecules necessary for translation or transcription-coupled translation thus enhancing expression yields for a particular gel or gels.

In one embodiment, the hollow "close ended" networked matrix enhances the protein yield 1, 2, 3, 4, 5, 6, 7, 8, 9, or 10-fold as compared to an open matrix. In some embodiments, the protein yield is enhanced more than 10-fold. In some embodiments, molds are used with multiple cavities and internal structures.

In another aspect, the nucleic acid hydrogels of the present invention are linked to at least one (or more) copolymer or additional compound, which are known in the art or described herein above. The nucleic acid molecules are capable of undergoing various enzymatic reactions, including DNA polymerase, RNA reverse transcriptase, terminal transferase, DNA ligase, RNA ligase, exonuclease, ribonuclease, endonuclease, polynucleotide kinase, DNA methylase, and DNA ubiquitinase. Therefore, the nucleic acid molecules can be readily modified or linked to said copolymer(s) or additional compound(s).

In some embodiments, the protein yielding matrixes yield protein at a rate of at least about 10, 15, 20, 25, 30, 35, 40, or 45 ng protein per 1 ng DNA or 1 ng RNA.

Another aspect of the invention is directed to nucleic-acid based protein-yielding matrixes where the resulting protein is post-translationally modified. Glycosylation in most eukaryotes occurs commonly in the endoplasmic reticulum (ER), i.e., yeast, insect, plant and mammalian cells share the features of N-linked oligosaccharide processing in the ER. Though the resultant glycoproteins in the ER have a near identical carbohydrate structure, with only the initial glycosylation in the ER, it can be difficult to produce glycoproteins with therapeutic efficacy. In various embodiments, a hydrogel can comprise the macromolecules necessary for post-translational modification of proteins produced in the cell-free protein synthesis system of the invention.

The production of premature glycoprotein, which does not undergo the complete post-translational modification, may be caused by the deficiency of the terminal glycosylation machinery such as the Golgi apparatus. In other words, oligosaccharide processing by different cell types may diverge in the Golgi apparatus. The initial step in O-glycosylation by mammalian cells is the covalent attachment of N-acetylgalactosamine to serine or threonine. No O-glycosylation sequence has been identified analogous to the Asn-X-Ser/Thr template required for N-glycosylation. In further contrast to N-glycosylation, no preformed, lipid-coupled oligosaccharide precursor is involved in the initiation of mammalian O-glycosylation. Sugar nucleotides serve as the substrates for the first and all subsequent steps in O-linked processing. Following the covalent attachment of N-acetylgalactosamine to serine or threonine, several different processing pathways are possible for mammalian O-linked oligosaccharides in the Golgi. The oligosaccharide structures of glycoproteins can have a profound effect on properties critical to the human therapeutic use, including plasma clearance rate, antigenicity, immunogenicity, specific activity, solubility, resistance to thermal inactivation, and resistance to protease attack. Therefore, for a cell-free protein synthesis to be applied to the large-scale production of glycoprotein and for a rapid insight into the role of protein glycosylation to understand the relationship among stability, conformation, function of protein and glycosylation, an efficient cell-free completely post-translationally modified protein synthesis system in which protein is completely post-translationally modified can be implemented using the protein-yielding matrixes described herein.

For the production of proteins having the complete and correct structure, the present invention includes the combination of a cell-free protein synthesis system and co- and post-translational modification machinery containing organelles, separated from cells, relevant to co- and post-translational modification. This method is suitable especially to large-scale production of efficacious and useful proteins. Additionally, this method can be applied directly to post-translational modification processes, required to produce a biologically active protein besides glycosylation.

As mentioned above, since the addition of only the ER cannot produce the completely post-translationally modified proteins, the addition of co- and post-translational modification machinery involved in terminal glycosylation is necessary. The addition of co- and post-translational modification machinery containing signal recognition particle, ER, Golgi apparatus, plasma membrane, and the like to the cell-free protein synthesis reaction mixture stimulates the production of completely post-translationally modified protein. A complete incubation mixture (containing the components of cell-free protein synthesis and co- and post-translational modification machinery) gives the completely post-translationally modified proteins. The events of the co- and post-translational modification process can be faithfully reproduced in vitro.

Cell sources for the preparation of the extract or lysate for the cell-free protein synthesis system and those for the co- and post-translational modification machinery may be the same or different. In the case of using the same cell, the extract or lysate for the cell-free protein synthesis system and the co- and post-translational modification machinery may be prepared separately or together. Examples for methods of preparing such extracts are known in the art, as described in U.S. Pat. No. 6,780,607, which is incorporated by reference herein in its entirety.

The co- and post-translational modification machinery may be prepared from tissues and cultured cell lines. In glycosylation it is favorable to genetically engineer a cell source for the enhancement of the expression level of glycosylation related enzymes and/or for the enrichment of the pool of sugar nucleotides which serve as sugar donors in glycosylation. This type of genetic manipulation can be carried out by those skilled in the art; therefore, the detailed explanation is omitted in this specification.

As an example for obtaining the cell extract in the cell-free protein synthesis method, the preparation of nuclease-treated RRL and a crude homogenate from Chinese hamster ovary (CHO) cells, as well as the preparations of ER containing signal recognition particle, Golgi apparatus, and plasma membrane from a crude homogenate are described in detail in U.S. Pat. No. 6,780,607. Such extracts can be obtained from any appropriate mammalian cell(s).

A glycoprotein produced by cell-free protein synthesis using the hydrogel matrices of the invention may be further modified through carbohydrate-adding reaction and/or carbohydrate-deleting reaction and/or carbohydrate-substituting reaction with enzymes relevant to the modification of side chains, e.g., glycosyltransferase, glycosidase, transglycosidase and so on. As such the addition, deletion, or substitution of carbohydrate side chains is effected. Furthermore, in another embodiment, one or more protein-yielding matrixes, in conjunction with the necessary macromolecules, can produce proteins with carbohydrate side chains not known in the general glycoprotein structures or produce novel glycoprotein structures synthesized artificially, and thus resulting in development of new glycoproteins. For example, in the carbohydrate-adding reaction resultant itself or the erythropoietin (EPO) separated from it, sialic acid is further attached to the terminal chain thereof by transglycosidase which is one of carbohydrate chain addition enzymes, and the efficacy of glycoprotein increases with the addition of sialic acid to the terminal chain thereof.

Therefore, in some embodiments, the protein-yielding matrixes can be applied to the production of proteins of therapeutic, commercial or research value. This includes proteins such as growth hormones, granulocyte colony stimulating factor, interleukin, interferon, thrombopoietin, tissue plasminogen activator and humanized monoclonal antibody. Additionally, in certain embodiments, kits are provided comprising nucleic acid matrixes for protein production of completely post-translationally modified protein as well as the necessary extracts discussed above that are necessary for post-translational modification thus enabling a research tool in the form of a co- and post-translational modification to analyze protein functionality.

In other aspects of the invention, the protein yielding matrixes can be re-used at least 3 times and can for at least days before the gel micropads are degraded by nucleases (e.g., from lysates). However, by linking the nucleic acid based matrices of the invention with at least one copolymer or at least one additional compound, matrices can be constructed that are mechanically stronger gels. In one embodiment, doping with gold nanoparticles (AuNP) is utilized to make stronger gels, where gold is attached either onto the DNA strands by direct crosslinking AuNP with DNA or between DNA strands by suspending AuNP in the gel. In addition, nuclease activity can be significantly reduced by adding compounds known in the art (such as DNase, Exo Nuclease III, etc.), or achieved by either conventional protein fractions or by passing through Ab-affinity columns to further purify extracts utilized for in vitro protein expression.

In another aspect of the invention, the nucleic acid hydrogels are further stabilized against degradation by modifications of the nucleic acid backbone. Such modifications are described herein or known in the art, such as those disclosed in U.S. Patent Publication Nos. 2005/32068, 2004/161844, 2001/49436, and U.S. Pat. Nos. 5,610,289; 5,965,721; 6,201,103 (teaching Peptide Nucleic Acid comprising modified backbone), or 6,025,482, the disclosure of each of which is incorporated herein by reference.

In yet another aspect, the nucleic acid hydrogels are further stabilized by linking nucleic acids of the matrix to a copolymer, which are known in the art or described herein above. In one embodiment, a branched DNA-polystyrene hybrid molecule is constructed. Therefore, some embodiments, a P-gel is constructed either entirely from a nucleic acid-copolymer hybrid molecule or from a mixture of nucleic acid and nucleic acid-polystyrene. The nucleic acid can be DNA. This method provides a hybrid nucleic acid P-gel whose backbone consists of a nuclease-resistant polystyrene group. As such, the matrices are significantly strengthened and become amenable to recycling. Thus, in one embodiment the protein yielding matrices can be re-used 1, 2, 3, 4, 5, 6, 7, 8, 9, 10, 11, 12, 13, 14, or 15 times. In some embodiments, the protein yielding matrices can be re-used more than 15 times. Additional copolymers that can be linked to nucleic acids are disclosed herein.

EXAMPLE 1

Chemicals and DNA Sequences:

Enzymes were purchased from New England Biolabs, Beverly, Mass. Oligonucleotides were commercially synthesized and PAGE purified (Integrated DNA Technologies, Coralville, Iowa). Sequences of the oligonucleotides are:

```
Circular Template (SEQ ID NO. 1):
5'-Phosphate-TCGTTTGATGTTCCTAACGTACCAACGCACACGCAGT

ATTATGGACTGGTAAAAGCTTTCCGAGGTAGCCTGGAGCATAGAGGCATT

GGCTG

Primer 1 (SEQ ID NO. 2):
5'-CAGTCCATAATACTGCGT
(complementary to circular template)

Primer 2 (SEQ ID NO. 3):
5'-ACGCAGTATTATGGACTG

Primer 3 (SEQ ID NO. 4):
5'-TGGTACGTTAGGAACATC
(complementary to circular template)
```

Preparation of Circular Templates:

Two hundred microliter of ligation reaction mixture (0.5 µM of ssDNA linear template, 50 µM of ATP, 2.5 mM of $MnCl_2$, 5 unit/µL of CircLigase ssDNA Ligase in a reaction buffer provided) was incubated overnight at 65° C. This solution was heated up at 80° C. for 10 minutes ("min") to inactivate the CircLigase then gradually cooling down to 4° C. To remove the non-circularized linear ssDNA template, 300 U of Exonuclease I and 3,000 U of Exonuclease III were added to the solution. This solution was incubated at 37° C. for 3 hrs and was then incubated at 80° C. for 40 min followed by the gradual cooling down step to inactivate the Exonucleases.

Hybridize Primer with Circular Templates:

Equimolar of primer 1 and circular DNA were hybridized for 2 hours at room temperature.

Gelation of Gel 1 by Rolling Circle Amplification:

Gelation 1: 10 nM of circular templates were incubated with Φ29 DNA polymerase (1 unit/μL) at 30° C. for 4 hrs (the final solution contained 50 mM Tris-HCL, 10 mM $(NH_4)_2SO_4$, 10 mM $MgCl_2$, 4 mM dithiothreitol, 200 μg/ml bovin serum albumin, 50 mM dNTP). Gelation 2: 10 pM of primer 2 and primer 3 were added into the same solution after gelation 1 and then the solution was incubated overnight at 30° C.

Gel Electrophoresis:

ssDNA linear DNA before circularization and circular template DNA were run in 10% denaturing PAGE gel at 600 volts at 25° C. for 1 hour with Tris-borate-EDTA (TBE, pH 8.3). The gel was stained using the gel stain SYBR II (Molecular Probes, Oregon) following the manufacturer's protocol.

EXAMPLE 2

Figure 2:
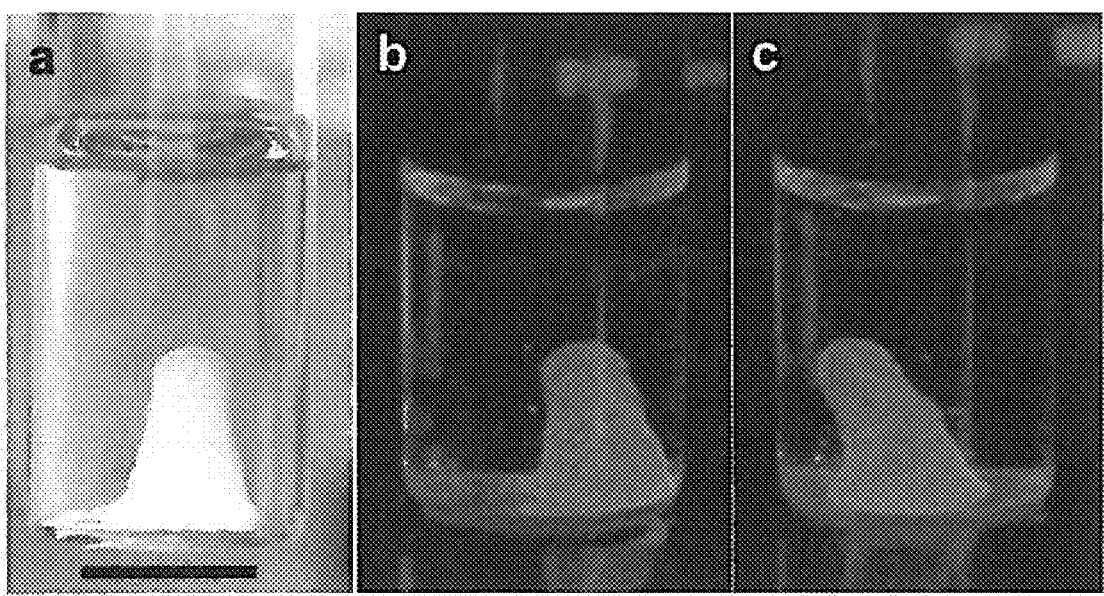
FIG. 2 shows DNA hydrogels formed by RCA, in accordance with an embodiment of the invention.

With reference to FIG. 2, DNA hydrogels made entirely from the product of rolling circle amplification are shown. A swollen DNA hydrogel in water (left) and stained DNA hydrogel with GelGreen, DNA-specific fluorescent dyes (right) are shown. The scale bars are 10 mm.

With continued reference to FIG. 2, the DNA hydrogel comprises entangled RCA products. A DNA-specific fluorescent dye (GelGreen) was used to stain the gel. The stained DNA hydrogel gave out green fluorescence, strongly suggesting that the hydrogel was composed of DNA molecules which were produced by rolling circle amplification (FIG. 2b, c).

EXAMPLE 3

Figure 3:
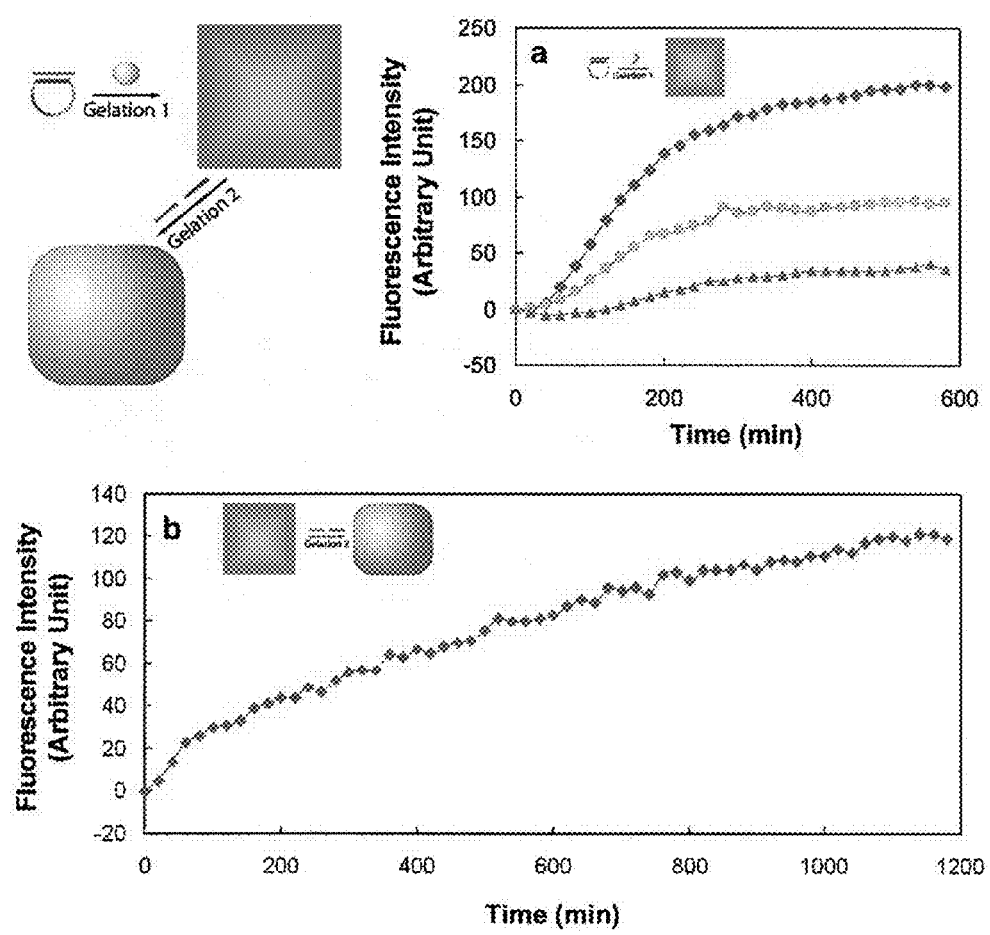
FIG. 3 shows gelation profiles and fluorescence intensity, in accordance with an embodiment of the invention.

With reference to FIG. 3, gelation profiles based on the fluorescence intensity are shown, in accordance with an embodiment of the invention. FIG. 3a shows a profile of the first gelation step (gelation 1) with three different conditions using 10 nM circular RCA templates and 1 unit/μL of Φ29 DNA polymerase (♦), 2 nM circular RCA templates and 1 unit/μL of Φ29 DNA polymerase (●), and 10 nM circular RCA templates and 0.2 unit/μL of Φ29 DNA polymerase (▲). FIG. 3b shows a profile of the second gelation step (gelation 2) by adding 10 pM of a second and third primer (primer 2 and primer 3) after gelation 1 of the conditions with 10 nM circular RCA templates and 1 unit/μL of Φ 29 DNA polymerase (♦).

FIG. 3 shows the results of the changes in fluorescence intensity with time during the gelation process. There was an increase in fluorescence intensity during gel aging because Φ29 DNA polymerase generated long amplified DNA. In the gelation 1, the increase of fluorescence intensity reached a maximum after about 9 hours (see FIG. 3a). The result indicates that long single stranded DNA (ssDNA) was slowly produced for 9 hours. As can be seen in FIG. 3a, most of gelation 1 was finished within 4 hours. With 5-fold less circular RCA template (2 nM), the fluorescence intensity increased up to half of the gelation 1 with 10 nM circular RCA templates. With a 5-fold reduction in the concentration of Φ29 DNA polymerase, the increase of fluorescence intensity was concomitantly about 5-fold less. FIG. 3b shows that the fluorescence intensity slowly increased during the gelatin 2 process for about 18 hours. Without adding fresh Φ29 DNA polymerase, long ssDNA in gelation 1 were repeatedly converted to double-stranded DNA (dsDNA) and separated to ssDNA resulting in increase of fluorescence intensity.

EXAMPLE 4

Figure 4:
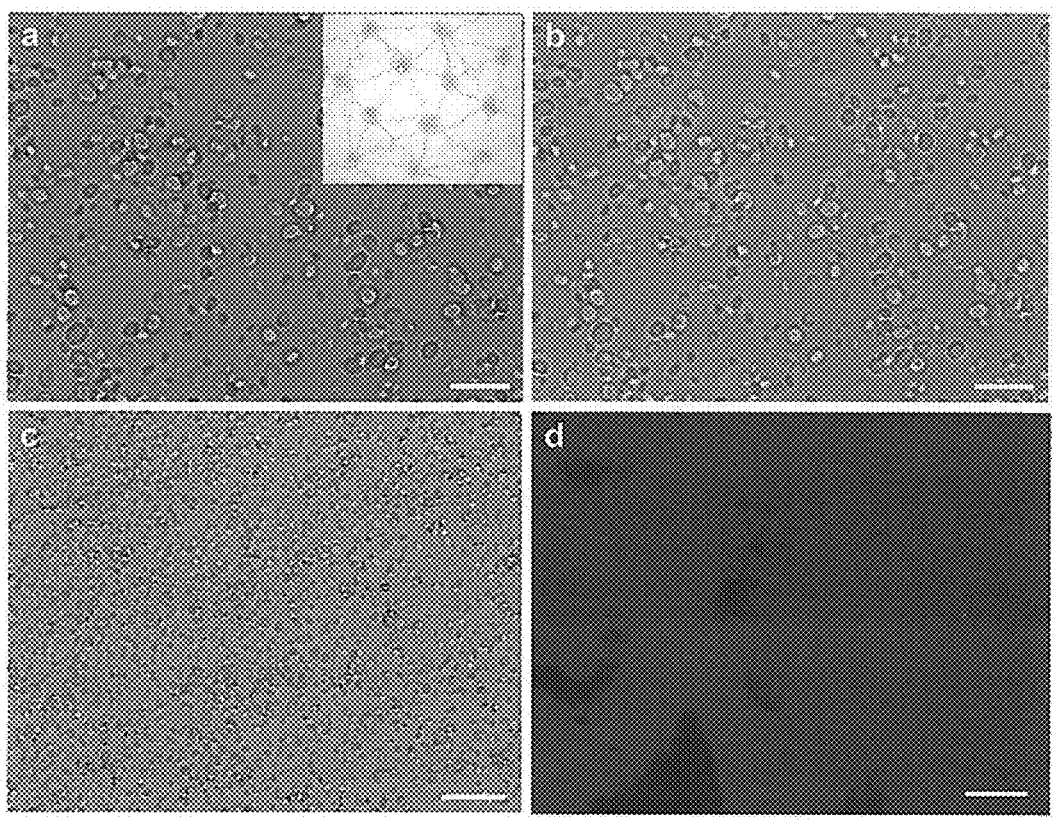
FIGS. 4a-d show microscopic images of DNA hydrogels, in accordance with an embodiment of the invention.

FIG. 4 shows microscopic images of DNA Hydrogels. FIGS. 4a and 4c show differential interference contrast ("DIC") images of DNA hydrogel at different magnification and a schematic drawing (FIG. 4a, inset). FIG. 4b shows the overlay of DIC and fluorescence images. FIG. 4d shows fluorescence microscopic image of the DNA hydrogel. The scale bars are 10 μm for FIGS. 4a and 4b, 20 μm for FIG. 4c, 100 μm for FIG. 4d.

To investigate the internal structure of the hydrogel based on DNA entanglement, DIC and fluorescence microscopy were used to obtain the images of FIG. 4. The hydrated DNA gel was composed of several micrometer-sized entanglement (between about 1 μm and 5 μm) of amplified DNA (FIG. 4a). The result indicates that the amplified DNA products were entangled to each other to be connected physically, and that the heavy entanglements caused the micron-sized DNA-based ball of thread which is illustrated in the inset of FIG. 4a. This ball of DNA thread has similar structure of relaxed flagelliform protein of spider capture silk (*Nat. Mat.* 2, 278-283 (2003)), allowing for considerable elongation generating elasticity. The loose DNA thread in the balls can be extended by stretching force for generating elasticity. In FIG. 4b, the overlay image of DIC and fluorescence microscopy indicates that the ball is the DNA product of RCA. The balls of DNA thread (circular or nearly circular objects in FIG. 4b) were stained to emit bright green fluorescence light with a DNA-specific fluorescent dye. Although, the extended linear DNA were not shown in DIC images because of resolution limit of microscope, entire green fluorescence background in FIG. 4b (color not shown in the grayscale image) indicated that the ball of DNA thread were connected by a variety of entangled linear DNA with spider web-like structure. Low magnification DIC image in FIG. 4c shows more balls of DNA thread. FIG. 4d shows fluorescence microscope image of a half millimeter region of the gel which is densely connected by amplified DNA.

EXAMPLE 5

Figure 5:
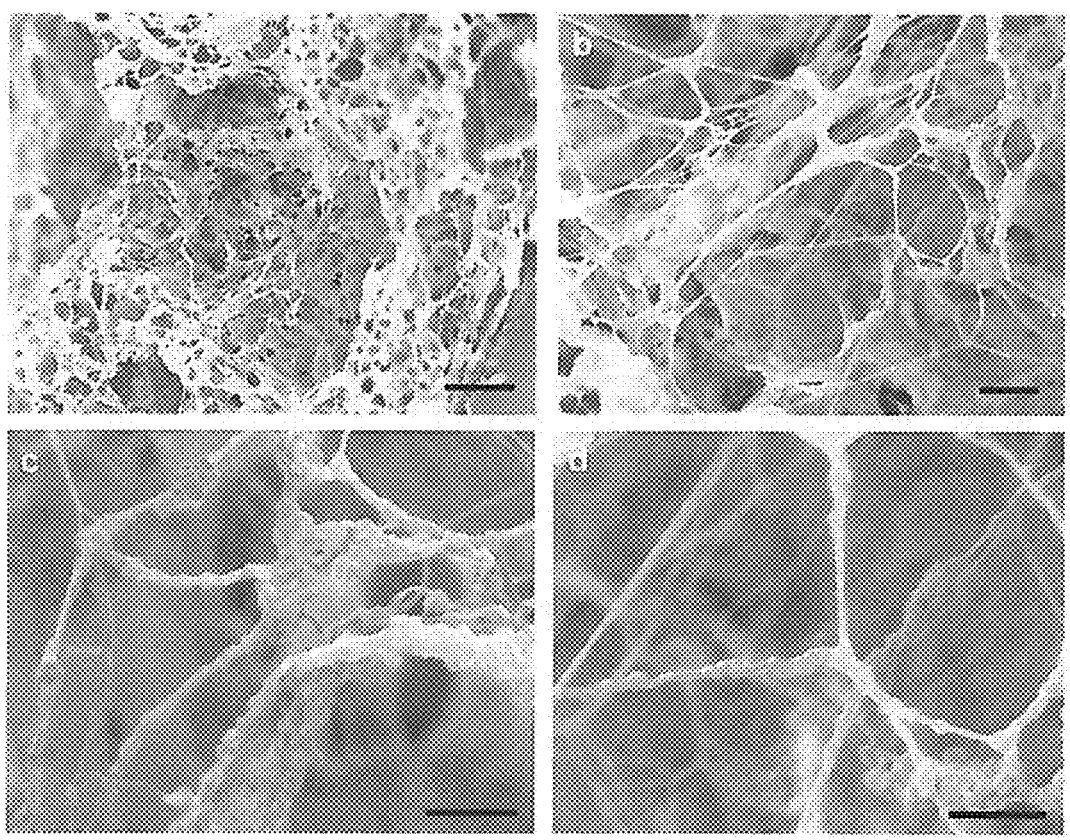
FIGS. 5a-d show microscopic images of DNA hydrogels, in accordance with an embodiment of the invention.

FIG. 5 shows scanning electron microscopy images (or micrographs) of dried DNA Hydrogels. Images at various magnification of DNA hydrogel are indicated. The scale bars are 100 μm for FIG. 5a, 20 μm for FIG. 5b, and 10 μm for FIGS. 5c and 5d.

To elucidate the physical structure of DNA hydrogel, the surface morphology was studied in dried state using scanning electron microscopy ("SEM"). In a dry state, the morphology revealed a pattern similar to that of a spider web (FIGS. 5a and 5b). These spider web-like structures are composed of small fibrils that interconnect the larger fibers. High magnification SEM images in FIGS. 5c and 5d showed that the fibers were approximately 1-3 μm in diameter. The several micron diameter DNA fibers suggest that the number of amplified long DNA in 2 nm diameter is heavily entangled together.

EXAMPLE 6

Figure 6:
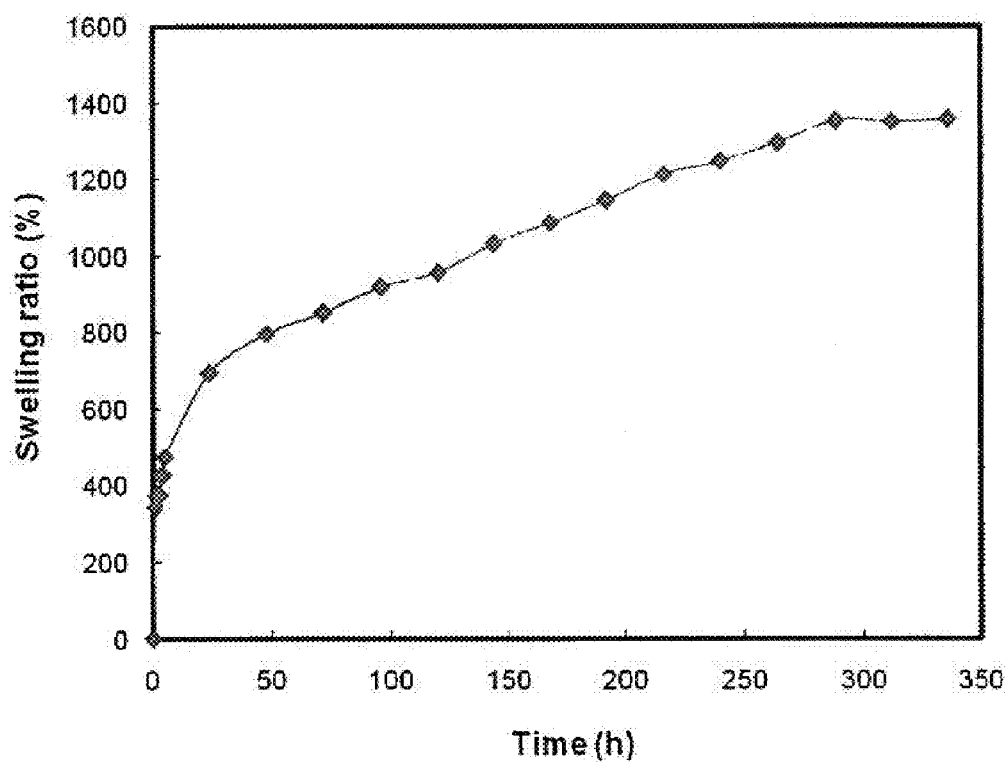
FIG. 6 illustrates a plot of the Swelling ratio (%) of a hydrogel as a function of Time (h), in accordance with an embodiment of the invention.

FIG. 6 shows a plot of the swelling ratio (%) of DNA hydrogel. The swelling was confirmed in MilliQ water from the dry state for 300 h. The swelling ratio of DNA hydrogel was investigated with the gel in MilliQ water from dry state for 336 h (14 days). The swelling ratio was determined as $[(W_s-W_d)/W_d] \times 100\%$, wherein $W_s$ is the weight of the swollen DNA gel, $W_d$ is the weight of the dry DNA gel. As can be seen in FIG. 6, the DNA gel swelled up to 700% in one day; however, the swelling ratio increased gradually to reach the equilibrium swelling ratio of about 1350% within 11 more days. This latter swelling process was due to the highly entangled nature of the long DNA. In some embodiments, the DNA hydrogel can provide ideal swelling properties for controlled release, which exhibit sustained release over long periods of time.

EXAMPLE 7

Figure 7:
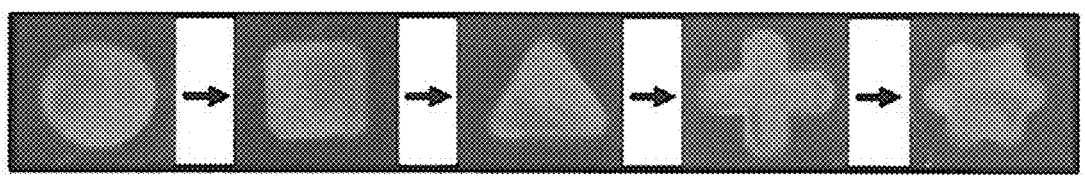
FIG. 7 shows the flexibility of DNA hydrogel by molding the hydrogel into a variety of shapes, in accordance with an embodiment of the invention.

FIG. 7 shows the flexibility of DNA Hydrogel. A swollen DNA hydrogel was located in five molds having different shapes (i.e., circular/round, boxlike, triangular, cross and star).

Due to the flexibility, the shape of the swollen DNA hydrogel is dependent on the shape of mold. The round shaped DNA hydrogel was transformed to rectangular, triangle, cross, and star shape (FIG. 7). The gel remained intact during the transformation because of the highly entangled nature to prevent denaturing by physical force.

EXAMPLE 8

Figure 8:
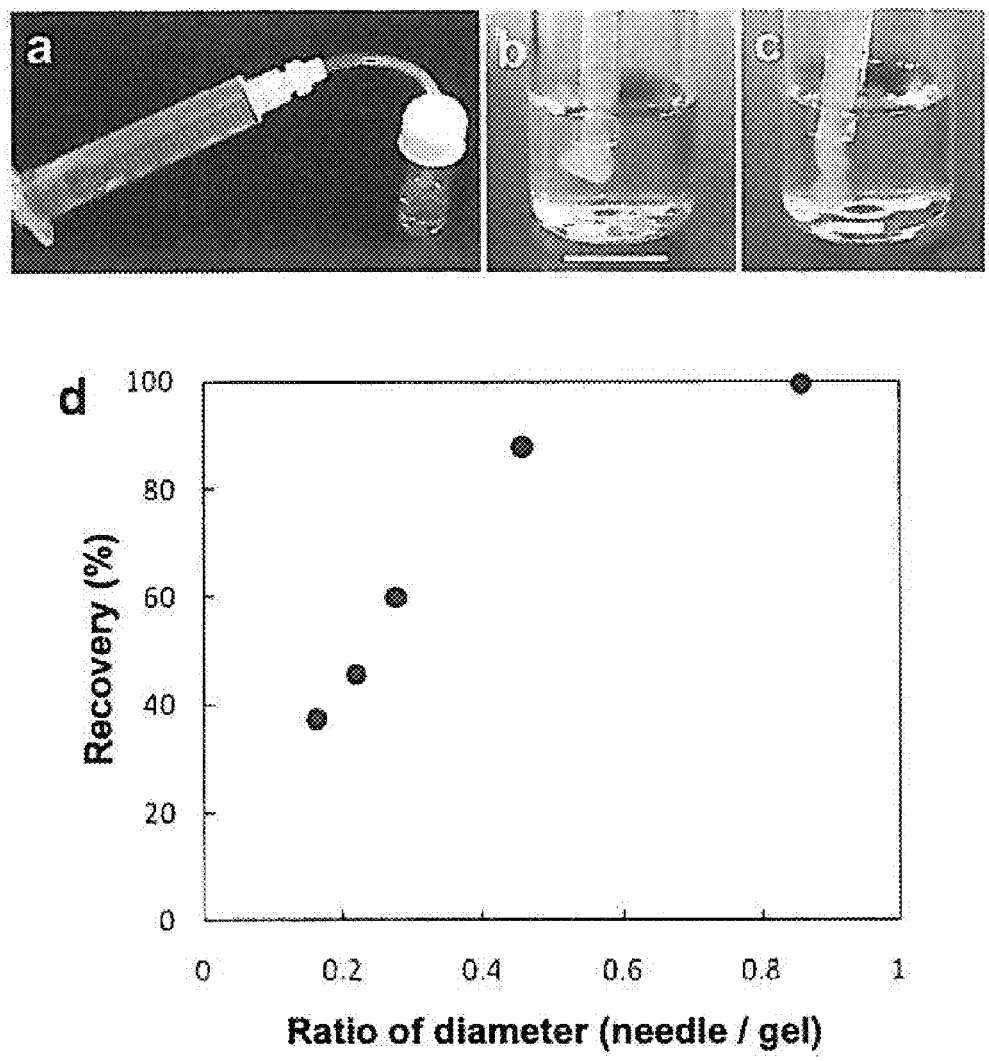
FIG. 8a illustrates an image of DNA hydrogel injection.
FIGS. 8b and 8c show a DNA hydrogel after passage through a needle.
FIG. 8d is a plot of recovery (%) vs. the ratio of diameter (needle/gel), in accordance with an embodiment of the invention.

FIG. 8 shows injecting a DNA hydrogel with different size needles. FIG. 8a shows Images of DNA hydrogel injection. FIGS. 8b and 8c show the DNA hydrogel after passing through the narrow needle. The scale bar is 1 cm. FIG. 8d shows the recovery length from the original length (plotted as a percentage, %) of DNA hydrogel plotted against the ratio of diameter needle and gel.

To investigate the usability of DNA hydrogel for injection, five different size of needle were used. Although the shape of the gels was elongated after injection, the gel remained intact up to using 23G needle (FIGS. 8a, 8b, and 8c). Because of the robustness, the gel could be used for perfect biocompatible drug carrier with high localized drug by injection. In addition, the DNA hydrogel had relatively good elastic properties showing the elongated gel tended to return to its original shape (FIG. 8d). With five times less diameter needle than DNA gel, the deformed gel recovered their length to about 40% of their original length.

While preferable embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A composition comprising a nucleic acid hydrogel, the nucleic acid hydrogel comprising entangled single-stranded nucleic acid molecules, wherein at least a portion of the single-stranded entangled nucleic acid molecules are formed via rolling cycle amplification, and further wherein said nucleic acid hydrogel has a matrix for structural support, wherein said matrix is formed by gelation of said single-stranded entangled nucleic acid molecules and water, wherein the gelation occurs from a mixture consisting essentially of at least one single-stranded entangled nucleic acid molecule and water.

2. A composition comprising a nucleic acid hydrogel, the nucleic acid hydrogel comprising:
   a first single-stranded nucleic acid molecule, the first single-stranded nucleic acid molecule formed from the amplification of a circular nucleic acid template using a first primer; and
   a second single-stranded nucleic acid molecule, the second single-stranded nucleic acid molecule formed from the amplification of the first single-stranded nucleic acid molecule using a second primer,
   and further wherein said nucleic acid hydrogel has a matrix for structural support, wherein said matrix is formed by gelation of said single-stranded nucleic acid molecules and water, wherein the gelation occurs from a mixture consisting essentially of at least one first single-stranded nucleic acid molecule, at least one second single-stranded nucleic acid molecule, and water.

3. A composition comprising a nucleic acid hydrogel, the nucleic acid hydrogel comprising:
   a first single-stranded nucleic acid molecule, the first single-stranded nucleic acid molecule formed from the amplification of a circular nucleic acid template using a first primer; and
   a second single-stranded nucleic acid molecule, the second single-stranded nucleic acid molecule formed from the amplification of the first single-stranded nucleic acid molecule using a second primer, and
   further comprising a third single-stranded nucleic acid molecule, the third single-stranded nucleic acid molecule formed from the amplification of the second single-stranded nucleic acid molecule using a third primer,
   and further wherein said nucleic acid hydrogel has a matrix for structural support, wherein said matrix is formed by gelation of at least one first single-stranded nucleic acid molecule, at least one second single-stranded nucleic acid molecule, at least one third single-stranded nucleic acid molecule, and water, wherein the gelation occurs from a mixture consisting essentially of at least one first single-stranded nucleic acid molecule, at least one second single-stranded nucleic acid molecule, at least one third single-stranded nucleic acid molecule, and water.

4. The composition nucleic acid hydrogel of claim 3, wherein the third primer is complementary to a portion of the circular nucleic acid template.

5. The composition nucleic acid hydrogel of claim 3, wherein the third primer is complementary to a portion of the second single-stranded nucleic acid molecule.

6. The composition nucleic acid hydrogel of claim 3, wherein the third single-stranded nucleic acid molecule is entangled with one or both of the first single-stranded nucleic acid molecule and the second single-stranded nucleic acid molecule.

7. The composition nucleic acid hydrogel of claim 2, wherein the first primer is complementary to a portion of the circular nucleic acid template.

8. The composition nucleic acid hydrogel of claim 2, wherein the first primer is complementary to the second primer.

9. The composition nucleic acid hydrogel of claim 2, wherein the second primer is complementary to a portion of the first single-stranded nucleic acid molecule.

10. The composition nucleic acid hydrogel of claim 2, wherein the second single-stranded nucleic acid molecule is entangled with the first single-stranded nucleic acid molecule.

11. The composition nucleic acid hydrogel of claim 2, wherein one or both of the first and second single-stranded nucleic acid molecules comprise deoxyribonucleic acid (DNA), ribonucleic acid (RNA), peptide nucleic acid (PNA), morpholino and locked nucleic acid (LNA), glycol nucleic acid (GNA) and/or threose nucleic acid (TNA).

12. A composition comprising a nucleic acid hydrogel, the nucleic acid hydrogel comprising:
   a first single-stranded nucleic acid molecule, the first single-stranded nucleic acid molecule formed from the amplification of a circular nucleic acid template using a first primer; and
   a second nucleic acid molecule,
   and further wherein said nucleic acid hydrogel has a matrix for structural support, wherein the matrix is formed by gelation of said single-stranded nucleic acid molecules and water, wherein the gelation occurs from a mixture consisting essentially of at least one first single-stranded nucleic acid molecule, at least one second nucleic acid molecule, and water.

13. The composition nucleic acid hydrogel of claim 12, wherein the second nucleic acid molecule is single-stranded.

14. The composition nucleic acid hydrogel of claim 12, wherein the second nucleic acid molecule is double-stranded.

15. A nucleic acid hydrogel, comprising:
- a first single-stranded nucleic acid molecule, the first single-stranded nucleic acid molecule formed from the amplification of a circular nucleic acid template using a first primer; and
- a second nucleic acid molecule;
- wherein the first nucleic acid molecule comprises DNA and the second nucleic acid molecule comprises RNA.

16. The composition nucleic acid hydrogel of claim 1, wherein said single-stranded entangled nucleic acid molecules are not crosslinked.

17. The composition nucleic acid hydrogel of claim 1, wherein a portion of said single-stranded entangled nucleic acid molecules are coding nucleic acid molecules.

18. The composition nucleic acid hydrogel of claim 1, wherein a portion of said single-stranded entangled nucleic acid molecules are non-coding nucleic acid molecules.

19. The composition nucleic acid hydrogel of claim 1, wherein said hydrogel further comprises one or more enzymes capable of macromolecules necessary for protein modification.

20. The composition nucleic acid hydrogel of claim 1, wherein said hydrogel is elastic.

21. The composition nucleic acid hydrogel of claim 1, wherein the hydrogel is capable of recovering a substantial amount of its original shape after passing the structural support is preserved after injection of the hydrogel through a needle.

22. The composition nucleic acid hydrogel of claim 1, further comprising a drug.

23. The nucleic acid hydrogel of claim 15, wherein the first single-stranded nucleic acid molecule is not crosslinked to the second nucleic acid molecule.

24. The nucleic acid hydrogel of claim 15, wherein the hydrogel further comprises one or more enzymes capable of macromolecules necessary for protein modification.

25. The nucleic acid hydrogel of claim 15, wherein the hydrogel is elastic.

26. The nucleic acid hydrogel of claim 15, wherein the first single stranded nucleic acid molecule and the second nucleic acid molecule are entangled.

27. The nucleic acid hydrogel of claim 15, wherein the hydrogel is capable of recovering a substantial amount of its original shape after passing the structural support is preserved after injection of the hydrogel through a needle.

28. The nucleic acid hydrogel of claim 15, further comprising a drug.

* * * * *

SEQUENCE LISTING

<160> NUMBER OF SEQ ID NOS: 4

<210> SEQ ID NO 1
<211> LENGTH: 92
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcgtttgatg ttcctaacgt accaacgcac acgcagtatt atggactggt aaaagctttc      60
cgaggtagcc tggagcatag aggcattggc tg                                    92

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cagtccataa tactgcgt                                                    18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acgcagtatt atggactg                                                    18

```
<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggtacgtta ggaacatc                                                       18
```